US008003639B2

(12) United States Patent
Priepke et al.

(10) Patent No.: US 8,003,639 B2
(45) Date of Patent: Aug. 23, 2011

(54) SUBSTITUTED PROLINAMIDES, THE PREPARATION THEREOF AND THE USE THEREOF AS PHARMACEUTICAL COMPOSITIONS

(75) Inventors: Henning Priepke, Warthausen (DE); Georg Dahmann, Attenweiler (DE); Kai Gerlach, Mittelbiberach (DE); Herbert Nar, Ochsenhausen (DE); Roland Pfau, Biberach (DE); Annette Schuler-Metz, Ulm (DE); Wolfgang Wienen, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 80 days.

(21) Appl. No.: 12/278,296

(22) PCT Filed: Feb. 13, 2007

(86) PCT No.: PCT/EP2007/051390

§ 371 (c)(1),
(2), (4) Date: Aug. 5, 2008

(87) PCT Pub. No.: WO2007/093595

PCT Pub. Date: Aug. 23, 2007

(65) Prior Publication Data

US 2009/0048231 A1 Feb. 19, 2009

(30) Foreign Application Priority Data

Feb. 14, 2006 (EP) .................................... 06101653

(51) Int. Cl.
*A61K 31/55* (2006.01)

(52) U.S. Cl. ................................... 514/217.01; 540/594

(58) Field of Classification Search ................... 540/594
See application file for complete search history.

(56) References Cited

FOREIGN PATENT DOCUMENTS

| | | | |
|---|---|---|---|
| CA | 2 520 893 | A1 | 10/2004 |
| CA | 2 529 453 | A1 | 12/2004 |
| CA | 2 549 589 | A1 | 6/2005 |
| CA | 2 561 057 | A1 | 10/2005 |
| WO | 2004/087695 | A1 | 10/2004 |
| WO | 2004/110433 | A1 | 12/2004 |
| WO | 2005/058817 | A1 | 6/2005 |
| WO | 2005/092849 | A1 | 10/2005 |

OTHER PUBLICATIONS

International Search Report for PCT/EP2007/051390 mailed Jun. 12, 2007.

*Primary Examiner* — James O Wilson
*Assistant Examiner* — Brian McDowell
(74) *Attorney, Agent, or Firm* — Michael P. Morris; Usha R. Patel; Edouard G. Lebel

(57) ABSTRACT

The present invention provides new substituted prolinamides of the general formula (I) in which D, L, E, G, J, M, $R^3$, $R^4$, $R^5$, and $R^{13}$ are defined as in claim 1, their tautomers, their enantiomers, their diastereomers, their mixtures and their salts, more particularly their physiologically tolerated salts with organic or inorganic acids or bases, which exhibit valuable properties.

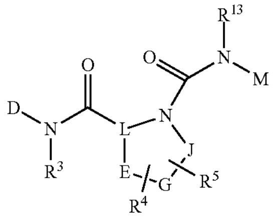

11 Claims, No Drawings

SUBSTITUTED PROLINAMIDES, THE PREPARATION THEREOF AND THE USE THEREOF AS PHARMACEUTICAL COMPOSITIONS

"This application is a national phase entry under 35 U.S.C. 371 of international application PCT/EP2007/051390, filed Feb. 13, 2007, which claims priority to European Application No. EP 06 100 653.1, filed Feb. 14, 2006, each of which is hereby incorporated by reference in its entirety."

The present invention relates to new substituted prolinamides of general formula (I)

(I)

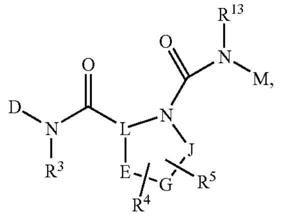

the tautomers, the enantiomers, the diastereomers, the mixtures and the salts thereof, particularly the physiologically acceptable salts thereof with inorganic or organic acids or bases, which have valuable properties.

The compounds of the above general formula (I) as well as the tautomers, the enantiomers, the diastereomers, the mixtures and the salts thereof, particularly the physiologically acceptable salts thereof with inorganic or organic acids or bases, and the stereoisomers thereof, have valuable pharmacological properties, particularly an antithrombotic activity and a factor Xa-inhibiting activity.

The present application relates to new compounds of the above general formula (I), the preparation thereof, the pharmaceutical compositions containing the pharmacologically effective compounds, the preparation and use thereof.

A first embodiment of the present invention encompasses those compounds of general formula (I), wherein D denotes a substituted bicyclic ring system of formula (II)

(II)

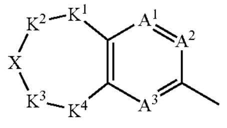

wherein $K^1$ and $K^4$ each independently of one another denote a —$CH_2$, —$CHR^{7a}$, —$CR^{7b}R^{7c}$, —C(=$CH_2$) or a —C(O) group, and wherein $R^{7a}/R^{7b}/R^{7c}$ each independently of one another denote a fluorine atom, a hydroxy, $C_{1-5}$-alkyloxy, amino, $C_{1-5}$-alkylamino, di-($C_{1-5}$-alkyl)amino, $C_{3-5}$-cycloalkyleneimino, $C_{1-5}$-alkylcarbonylamino group, a $C_{3-5}$-cycloalkyl or a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, while the two groups $R^{7b}/R^{7c}$ cannot both simultaneously be bound to the cyclic carbon atom via a heteroatom, except where —C($R^{7b}R^{7c}$)— corresponds to a —$CF_2$ group, or $R^{7a}$ denotes a fluorine-, chlorine-, bromine-, methyl-, methoxy-, amino- or nitro-substituted phenyl or monocyclic heteroaryl group, or two groups $R^{7b}/R^{7c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene-sulphide, hexamethyleneimine, 1,3-dioxolane, 1,4-dioxane, hexahydropyridazine, piperazine, thiomorpholine, morpholine, 2-imidazolidinone, 2-oxazolidinone, tetrahydro-2(1H)-pyrimidinone or [1,3]oxazinan-2-one ring, the methylene groups of which may be substituted by 1-2 $C_{1-3}$-alkyl or $CF_3$— groups, and/or the methylene groups of which, if they are not bound to a heteroatom, may be substituted by 1-2 fluorine atoms, and/or wherein a —$CH_2$ group adjacent to an N atom may be replaced by a —CO group, and/or the imino groups of which may in each case be substituted by a $C_{1-3}$-alkyl or $C_{1-3}$-alkylcarbonyl group, and/or wherein the sulphur atom may be oxidised to a sulphoxide or sulphone group, $K^2$ and $K^3$ each independently of one another denote a —$CH_2$, —$CHR^{8a}$, —$CR^{8b}R^{8c}$ or a —C(O) group, wherein $R^{8a}/R^{8b}/R^{8c}$ each independently of one another denote a $C_{3-5}$-cycloalkyl or a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, or two groups $R^{8b}/R^{8c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylene-sulphide, hexamethyleneimine, hexahydropyridazine, tetrahydro-2(1H)-pyrimidinone, [1,3]oxazinan-2-one ring, the methylene groups of which may be substituted by 1-2 $C_{1-3}$-alkyl or $CF_3$— groups, and/or the methylene groups of which, if they are not bound to a heteroatom, may be substituted by 1-2 fluorine atoms, and/or wherein a —$CH_2$ group adjacent to a nitrogen atom may be replaced by a —CO group, and/or the imino groups of which may in each case be substituted by a $C_{1-3}$-alkyl or $C_{1-3}$-alkylcarbonyl group, and/or wherein the sulphur atom may be oxidised to a sulphoxide or sulphone group, with the proviso that a heteroatom introduced by $R^{8b}$ or $R^{8c}$ must not be only one carbon atom away from X in formula (I), and in total a maximum of four groups selected from $R^{7a}$, $R^{7b}$, $R^{7c}$, $R^{8a}$, $R^{8b}$ and $R^{8c}$ may be present in formula (II), and X denotes an oxygen or sulphur atom, a $CF_2$, sulphene, sulphone or a $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl, oxetane-3-yl, tetrahydrofuran-3-yl, benzyl, $C_{1-5}$-alkyl-carbonyl, trifluoromethylcarbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)-aminocarbonyl, $C_{1-5}$-alkyloxycarbonyl, $C_{4-7}$-cycloalkyleneiminocarbonyl group, while the methylene and methyl groups present in the groups mentioned previously may additionally be substituted by a $C_{1-3}$alkyl, carboxy or $C_{1-5}$-alkoxycarbonyl group, or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not bound directly to a heteroatom selected from among O, N or S, and/or one to three hydrogen atoms may be replaced by fluorine atoms, provided that the methylene or methyl groups are not bound directly to a heteroatom selected from among O, N or S, and wherein $A^1$ denotes either N or $CR^{10}$, $A^2$ denotes either N or $CR^{11}$, $A^3$ denotes either N or $CR^{12}$, while $R^{10}$, $R^{11}$ and $R^{12}$ each independently of one another denote a hydrogen, fluorine, chlorine, bromine or iodine atom, or a $C_{1-5}$-alkyl, $CF_3$, $C_{2-5}$-alkenyl, $C_{2-5}$-alkynyl, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group, or D denotes one of the four groups (II-1), (II-2), (II-3), (II-4), (II-5) or (II-6)

(II-1)

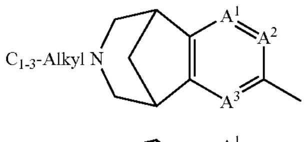

(II-2)

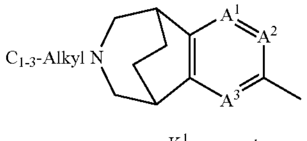

(II-3)

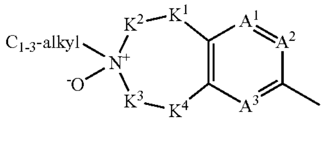

-continued (II-4)

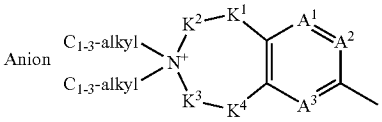

(II-5)

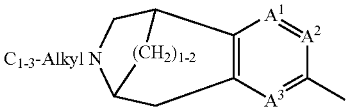

(II-6)

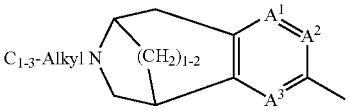

wherein the groups A1, A2, A3, K1, K2, K3, K4 are as hereinbefore defined, and the anion in (II-4) denotes a fluoride, chloride, bromide, iodide, sulphate, hydrogen sulphate, phosphate, hexafluorophosphate, hydrogen phosphate, benzoate, salicylate, succinate, citrate or tartrate, $R^3$ denotes a hydrogen atom or a $C_{1-3}$-alkyl group, and -L-E-G-J- denotes a —C—C—C—C or —C—C═C—C group, which may be substituted by $R^4$ and $R^5$, and $R^4$ denotes a hydrogen atom or a straight-chain or branched $C_{1-6}$-alkyl, $C_{2-6}$-alkenyl or $C_{2-6}$-alkynyl group, wherein the hydrogen atoms of the methylene and/or methyl fragments of the straight-chain or branched $C_{1-6}$-alkyl, $C_{2-6}$-alkenyl or $C_{2-6}$-alkynyl group may optionally be wholly or partly replaced by fluorine atoms, and/or wherein the hydrogen atoms of the methylene and/or methyl fragments of the straight-chain or branched $C_{1-6}$-alkyl, $C_{2-6}$-alkenyl or $C_{2-6}$-alkynyl group may optionally each be substituted independently of one another by one to two substituents selected from a $C_{3-5}$-cycloalkyl group, a nitrile, hydroxy or $C_{1-5}$-alkyloxy group, wherein the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, aminosulphonyl, $C_{1-5}$-alkylaminosulphonyl, di-($C_{1-5}$-alkyl)-aminosulphonyl, $C_{4-7}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino, $C_{3-6}$-cycloalkylcarbonylamino group, or a morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 $C_{1-3}$-alkyl or $C_{1-3}$-alkylcarbonyl groups or by 1-2 oxo groups, and/or wherein the hydrogen atoms of the $sp^2$-hybridised carbon atoms of the straight-chain or branched $C_{2-6}$-alkenyl group may optionally be wholly or partly replaced by fluorine atoms, or a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, or a phenyl, mono- or bicyclic heteroaryl, phenyl-$C_{1-5}$-alkyl or mono- or bicyclic heteroaryl-$C_{1-5}$-alkyl group, which may optionally be mono- to tri-substituted in the phenyl or heteroaryl moiety by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy and $C_{1-5}$-alkyloxycarbonyl group, and if -L-E-G-J- denotes a —C—C—C—C group, $R^4$ at E or G may also denote a fluorine atom or a hydroxy, $C_{2-5}$-alkenyloxy, $C_{2-5}$-alkynyloxy, $C_{1-5}$-alkyl-oxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, heteroaryl-$C_{0-3}$-alkyloxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino group, while the methyl or methylene groups present in the above-mentioned alkyl or cycloalkyl groups may each be substituted independently of one another by a substituent selected from among morpholinyl, thiomorpholinyl, pyrrolidinyl, piperidinyl, piperazinyl, tetrahydrofuranyl, tetrahydropyranyl, dimethylaminocarbonyl, $C_{1-3}$alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or that two atoms form an —O—O or —S—O— bond, is excluded, and $R^5$ denotes a hydrogen atom or a $C_{1-5}$ alkyl, $C_{2-5}$ alkenyl or $C_{2-5}$ alkynyl group, or if $R^5$ is linked to E or G it may also denote a hydroxy or methoxy group, or $R^4$ and $R^5$ if they are bound to the same carbon atom, may form a —C(O)—group, or a —C($F_2$)— group, or $R^4$ and $R^5$ if they are bound to the same carbon atom or to two adjacent carbon atoms, may form a $C_{3-7}$-cycloalkyl or $C_{5-7}$-cycloalkenyl group, wherein one of the methylene groups of this $C_{4-7}$-cycloalkyl group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or wherein two directly adjacent methylene groups of this $C_{4-7}$-cycloalkyl group may together be replaced by a —C(O)NH, —C(O)N($C_{1-5}$-alkyl), —S(O)$_2$NH, or —S(O)$_2$N($C_{1-5}$-alkyl) group, and/or wherein 1 to 3 carbon atoms of a $C_{3-7}$-cycloalkyl group may each optionally be substituted independently of one another by one or two fluorine atoms or one or two $C_{1-5}$-alkyl groups or a hydroxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group, with the proviso that a $C_{3-7}$-cycloalkyl group of this kind, formed from $R^4$ and $R^5$ together, wherein two heteroatoms in the cyclic group selected from among oxygen and nitrogen are separated from one another by precisely one optionally substituted —$CH_2$ group, and/or wherein two atoms in the ring form a —O—0 or —S—O— bond, is excluded, $R^{13}$ denotes a hydrogen atom or a $C_{1-5}$ alkyl group, M denotes a phenyl, thienyl or pyridyl ring optionally substituted by $R^2$ and $R^6$, wherein $R^2$ denotes a fluorine, chlorine, bromine or iodine atom or a methyl, ethyl, propyl, isopropyl, vinyl, methoxy, ethynyl, cyano or —C(O)$NH_2$ group, and $R^6$ denotes a hydrogen, fluorine, chlorine, bromine or iodine atom or a hydroxy, methoxy, trifluoromethoxy, an optionally fluorine-substituted $C_{1-3}$-alkyl, cyano, amino, or $NH_2C(O)$ group, while, unless otherwise stated, by the term "heteroaryl group" mentioned hereinbefore in the definitions is meant a monocyclic 5- or 6-membered heteroaryl group wherein the 6-membered heteroaryl group contains one, two or three nitrogen atoms, and the 5-membered heteroaryl group contains an imino group optionally substituted by a $C_{1-3}$-alkyl group, an oxygen or sulphur atom, or an imino group optionally substituted by a $C_{1-3}$-alkyl group or an oxygen or sulphur atom and additionally one or two nitrogen atoms, or an imino group optionally substituted by a $C_{1-3}$-alkyl group and three nitrogen atoms, and additionally a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms, and the bond is effected via a nitrogen atom or a carbon atom of the heterocyclic moiety or a fused-on phenyl ring, and wherein, unless otherwise stated, by the term "halogen atom" mentioned hereinbefore in the definitions is meant an atom selected from among fluorine, chlorine, bromine and iodine, and wherein unless stated otherwise the alkyl, alkenyl, alkynyl and alkoxy groups which have more than two carbon atoms, contained in the foregoing definitions, may be straight-chain or branched and the alkyl groups in the previously mentioned dialkylated groups, for example the dialkylamino groups, may be identical or different, and the hydrogen atoms of the methyl or ethyl groups contained in the foregoing definitions, unless stated otherwise, may be wholly or partly replaced by fluorine atoms, the tautomers, the enantiomers, the diastereomers, the mixtures thereof and the salts thereof.

Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thienyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzooxazolyl, benzo[c]isoxazolyl, benzo[d]-isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-5}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl or 2-ethyl-prop-2-en-1-yl group, Examples of the $C_{2-5}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl or 3-methyl-1-butyn-3-yl group.

A 2nd embodiment of the present invention encompasses those compounds of general formula (I), wherein E, G, J, L, M, $R^3$-$R^5$ and $R^{13}$ are defined as described in embodiment 1 and D denotes a substituted bicyclic ring system of formula (II)

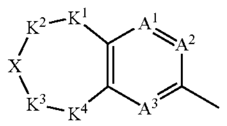

(II)

wherein $K^1$ and $K^4$ each independently of one another denote a —$CH_2$, —$CHR^{7a}$, —$CR^{7b}R^{7c}$, —C(=$CH_2$) or a —C(O) group, and wherein $R^{7a}/R^{7b}/R^{7c}$ each independently of one another denote a fluorine atom, a hydroxy, $C_{1-5}$-alkyloxy, a $C_{1-5}$-alkyl group, while the two groups $R^{7b}/R^{7c}$ cannot both simultaneously be bound to the cyclic carbon atom via a heteroatom, except where —$C(R^{7b}R^{7c})$— corresponds to a —$CF_2$ group, or two groups $R^{7b}/R^{7c}$ together with the cyclic carbon atom may form a cyclopropyl ring, $K^2$ and $K^3$ each independently of one another denote a —$CH_2$, —$CHR^{8a}$, —$CR^{8b}R^{8c}$ or a —C(O)— group, while $R^{8a}/R^{8b}/R^{8c}$ each independently of one another denote a $C_{1-5}$-alkyl group, or two groups $R^{8b}/R^{8c}$ together with the cyclic carbon atom may form a cyclopropyl ring, and in total a maximum of four groups selected from $R^{7a}$, $R^{7b}$, $R^{7c}$, $R^{8a}$, $R^{8b}$ and $R^{8c}$ may be present in formula (II), and X denotes an oxygen or sulphur atom, a sulphene, sulphone or an $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$ or a $C_{3-6}$-cycloalkyl group, and wherein $A^1$ denotes either N or $CR^{10}$, $A^2$ denotes either N or $CR^{11}$, $A^3$ denotes either N or $CR^{12}$, while $R^{10}$, $R^{11}$ and $R^{12}$ each independently of one another denote a hydrogen, fluorine, chlorine, bromine or iodine atom, or a $C_{1-5}$-alkyl, $CF_3$, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group.

A 3rd embodiment of the present invention encompasses those compounds of embodiments 1 or 2, wherein X denotes a $NR^1$ group, wherein $R^1$ denotes a hydrogen atom or a $C_{1-5}$-alkyl, allyl or cyclopropyl group, and $A^1$ denotes $CR^{10}$, $A^2$ denotes $CR^{11}$, $A^3$ denotes $CR^{12}$ while $R^{10}$, $R^{11}$ and $R^{12}$ each independently of one another represent a hydrogen, fluorine or chlorine atom, or a methyl, $CF_3$, hydroxy, methoxy, $CF_3O$, $CHF_2O$, $CH_2FO$ group.

A 4th embodiment of the present invention encompasses those compounds of general formula (I) wherein D, E, G, J, L, M, $R^3$ and $R^{13}$ are defined as described in embodiment 1, 2 or 3, and wherein $R^4$ denotes a hydrogen atom or a straight-chain or branched $C_{1-6}$-alkyl group, wherein the hydrogen atoms of the methylene and/or methyl fragments of the straight-chain or branched $C_{1-6}$-alkyl group may optionally be wholly or partly replaced by fluorine atoms, and/or wherein the hydrogen atoms of the methylene and/or methyl fragments of the straight-chain or branched $C_{1-6}$-alkyl group may optionally each be substituted independently of one another by a substituent selected from a hydroxy, $C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino, $C_{3-6}$-cycloalkylcarbonylamino group, or a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, and if -L-E-G-J- denotes a —C—C—C—C group, $R^4$ at E or G may also denote a fluorine atom or a hydroxy, $C_{2-5}$-alkenyloxy, $C_{2-5}$-alkynyloxy, $C_{1-5}$-alkyloxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino-group, while the methyl or methylene groups present in the above-mentioned alkyl or cycloalkyl groups may each be substituted independently of one another by a substituent selected from among dimethylaminocarbonyl, $C_{1-3}$alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or that two atoms form an —O—O or —S—O— bond, is excluded, and $R^5$ denotes a hydrogen atom, an allyl or a $C_{1-5}$ alkyl group, or if $R^5$ is linked to E or G it may also denote a hydroxy or methoxy group or $R^4$ and $R^5$, if they are bound to the same carbon atom, may form a —C(O)— group, or a —C($F_2$)— group, or $R^4$ and $R^5$ if they are bound to the same carbon atom or to two adjacent carbon atoms, may form a $C_{3-7}$-cycloalkyl group, wherein one of the methylene groups of this $C_{4-7}$-cycloalkyl group may be replaced by an oxygen or sulphur atom or an —NH, —N($C_{1-5}$-alkyl), —N($C_{1-4}$-alkylcarbonyl) or a carbonyl, sulphinyl or sulphonyl group, and/or wherein two directly adjacent methylene groups of this $C_{4-7}$-cycloalkyl group may together be replaced by a —C(O)NH, —C(O)N($C_{1-5}$-alkyl), —S(O)$_2$NH or —S(O)$_2$N($C_{1-5}$-alkyl) group.

A 5th embodiment of the present invention encompasses those compounds of embodiments 1, 2, 3 or 4 wherein -L-E-G-J- denotes a —C—C—C—C group which may be substituted by $R^4$ and $R^5$, which are defined as in embodiments 1, 2, 3 or 4 hereinbefore.

A 6th embodiment of the present invention encompasses those compounds of embodiments 1, 2, 3, 4 or 5, wherein D denotes a substituted benzazepinyl group of formula (IIa)

(IIa)

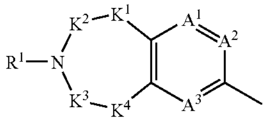

wherein $K^1$ and $K^4$ each independently of one another denote a —$CH_2$, —$CHR^{7a}$, —$CR^{7b}R^{7c}$ or a —C(O) group, wherein $R^{7a}$ denotes a $C_{1-5}$-alkyl, hydroxy or $C_{1-3}$-alkyloxy group and $R^{7b}/R^{7c}$ each independently of one another denote a hydroxy, $C_{1-5}$-alkyloxy or a $C_{1-5}$-alkyl group, while the two groups $R^{7b}/R^{7c}$ cannot both simultaneously be bound to the cyclic carbon atom via an oxygen atom, or two groups $R^{7b}/R^{7c}$ together with the cyclic carbon atom may form a cyclopropyl ring, and $K^2$ and $K^3$ each independently of one another denote a —$CH_2$, —$CHR^{8a}$ or —$CR^{8b}R^{8c}$ group, wherein $R^{8a}/R^{8b}/R^{8c}$ each independently of one another denote a $C_{1-3}$-alkyl group, and in total a maximum of four groups selected from $R^{7a}$, $R^{7b}$, $R^{7c}$, $R^{8a}$, $R^{8b}$ and $R^{8c}$ may be present in formula (II), and $R^1$ denotes a hydrogen atom or a $C_{1-5}$-alkyl, allyl or cyclopropyl group, and wherein $A^1$ denotes $CR^{10}$, $A^2$ denotes $CR^{11}$, $A^3$ denotes $CR^{12}$ while $R^{10}$, $R^{11}$ and $R^{12}$ each independently of one another denote a hydrogen, fluorine or chlorine atom, or a methyl, $CF_3$, hydroxy, methoxy, $CF_3O$, $CHF_2O$, $CH_2FO$ group, and L-E-G-J- denotes a —C—C—C—C group which may be substituted by $R^4$ and $R^5$, and $R^3$ denotes a hydrogen atom, and $R^4$ denotes a hydrogen atom or a straight-chain or branched $C_{1-3}$-alkyl group, wherein the hydrogen atoms of the methylene and/or methyl fragments of the straight-chain or branched $C_{1-6}$-alkyl group may optionally be substituted independently of one another by a substituent selected from among a hydroxy, $C_{1-5}$-alkyloxy, carboxy, $C_{1-5}$-alkyloxycarbonyl group, or a $CF_3$, nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group, or if $R^4$ is bound to E or G it may also denote a fluorine atom or a hydroxy, methoxy, $C_{2-5}$-alkenyl-oxy, $C_{2-5}$-alkyloxy, methoxyethoxy, $HOCH_2CH(OH)CH_2$oxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy-group, $R^5$ denotes a hydrogen atom or a $C_{1-5}$ alkyl group, or if $R^5$ is linked to E or G it may also denote a hydroxy or methoxy group, or $R^4$ and $R^5$, if they are bound to the same carbon atom, may denote a C═O or a —$CF_2$ group, and $R^{13}$ denotes a hydrogen atom, M denotes a substituted phenyl ring

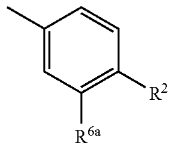

or a substituted pyridyl ring

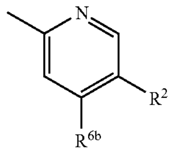

wherein $R^2$ denotes a fluorine, chlorine, bromine atom, a methoxy or ethynyl group, and $R^{6a}$ denotes a hydrogen or fluorine atom and $R^{6b}$ denotes a hydrogen atom.

According to the invention the compounds of general formula (I) are obtained by methods known per se, for example by the following methods:

(a) The preparation of a compound of general formula (III)

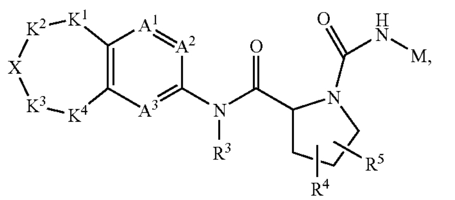

(III)

wherein $A^1$ to $A^3$, $K^1$ to $K^4$, M and $R^1$ to $R^6$ are defined as described in embodiment 1, and which may optionally be protected at any amino, hydroxy, carboxy or thiol groups by common protective groups such as for example those described in T. W. Greene, P. G. M. Wuts in "Protective Groups in Organic Synthesis", Wiley, 1991 and 1999, and the protective groups of which may be cleaved by methods known from the literature, is described in the examples or may be carried out for example according to the following formula schemes 1 and 2 or analogously to the methods of synthesis described in WO2004/87695, WO2004/87646 or in WO2003/45912.

Scheme 1

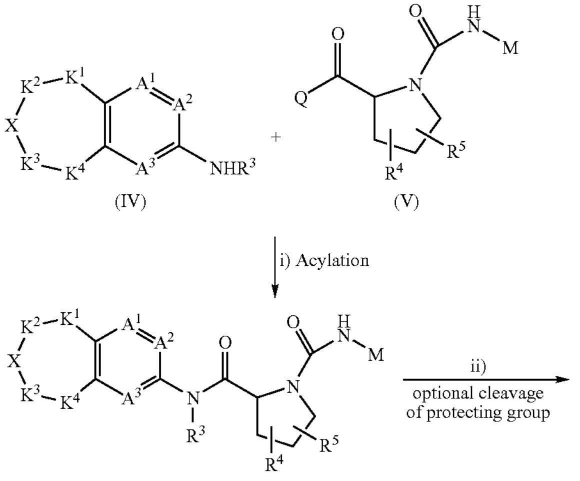

(IV) (V)

(IIIa)

Compound of Formula (III)

Scheme 2

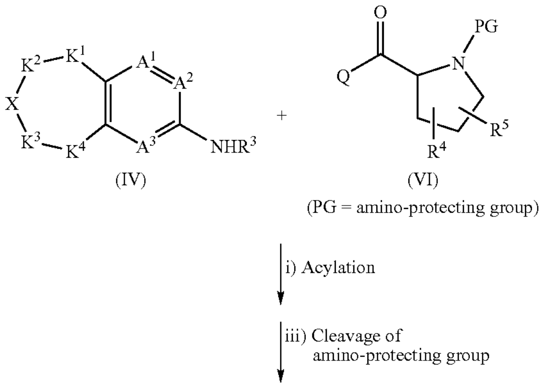

(IV) (VI)

(PG = amino-protecting group)

-continued

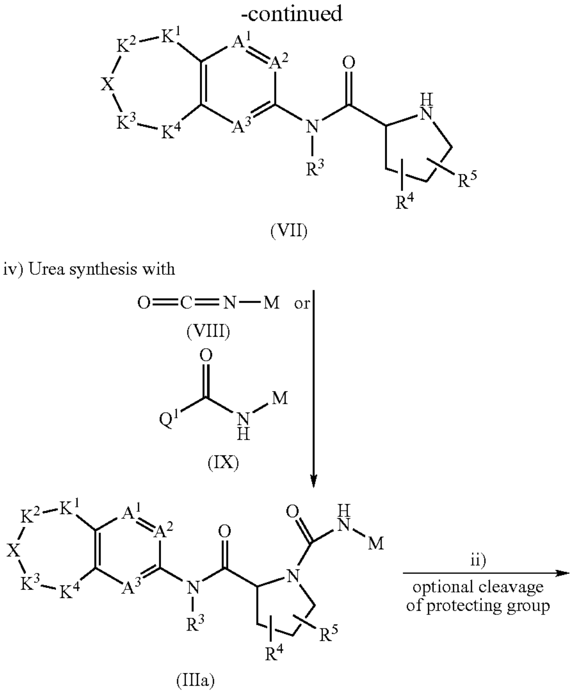

(VII)

(VIII)

(IX)

(IIIa)

Compound of Formula (III)

wherein $Q/Q^1$ denotes a leaving group or a group which may be converted in-situ into a leaving group, such as for example a halogen atom, a hydroxy, $C_{1-4}$-alkyloxy, alkyloxycarbonyloxy, 4-nitrophenyloxy, a trichloromethyl or acyloxy group, and PG denotes a protective group for the amino function known from the literature, such as for example a tert.-butoxycarbonyl, benzyloxycarbonyl or a trifluoroacetyl group.

The reaction steps i)-iv) shown in Schemes 1 and 2 may be carried out in the manner described in the Examples or according to the conditions known from the literature, for example as follows:

i) by acylating an amine (IV) with an optionally activated carboxylic acid (V) or (VI):

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, dimethylsulphoxide, sodium hydroxide solution or sulpholane, optionally in the presence of an inorganic or organic base at temperatures between −20 and 200° C., but preferably at temperatures between −10 and 100° C.

The acylation may however also be carried out with the free acid, optionally in the presence of an acid-activating agent or a dehydrating agent, for example in the presence of ethyl-1-ethoxy-1,2-dihydroquinoline-1-carboxylate, isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxybenzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-pentafluorophenyl-N,N,N',N'-tetramethyluronium-hexafluorophosphate/triethylamine, N,N'-thionyldiimidazole or triphenylphosphine/carbon tetrachloride, optionally with the addition of an auxiliary base such as sodium hydroxide solution, caesium, potassium or sodium carbonate or hydrogen carbonate or an amine base such as pyridine, triethylamine, N-methylmorpholine or diisopropylethylamine, at temperatures between −20 and 200° C., but preferably at temperatures between −10 and 160° C.

Other methods of amide coupling are described for example in P. D. Bailey, I. D. Collier, K. M. Morgan in "Comprehensive Functional Group Interconversions", Vol. 5, page 257ff., Pergamon 1995, or in the Houben-Weyl Supplementary Volume 22, published by Thieme, 2003, and the literature cited therein.

ii) or iii) Cleaving a protective group

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as tetrahydrofuran, methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

However, a protective group may also be cleaved by the methods described by T. W. Greene, P. G. M. Wuts in "Protective Groups in Organic Synthesis", Wiley, 1991 and 1999.

iv) Synthesis of a urea

The reaction of a derivative VII with an isocyanate VIII or an optionally activated carbamic acid IX is carried out in a solvent such as for example water, methylene chloride, chloroform, carbon tetrachloride, ether, tetrahydrofuran, dioxane, benzene, toluene, acetonitrile, dimethylformamide, dimethylsulphoxide or sulpholane or a mixture of the above-mentioned solvents, optionally with the addition of an auxiliary base such as sodium hydroxide solution, caesium, potassium or sodium carbonate or hydrogen carbonate or an amine base such as pyridine, triethylamine, N-methylmorpholine or diisopropylethylamine, at temperatures between −20 and 200° C., but preferably at temperatures between −10 and 160° C.

(b) The components of general formula (IV)

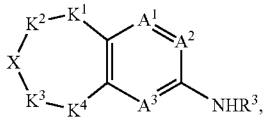

wherein $A^1$, $A^2$, $A^3$, $K^1$, $K^2$, $K^3$, $K^4$, X and $R^3$ are defined as in embodiment 1, and which may optionally be protected at any amino, hydroxy, carboxy or thiol groups present by common protective groups such as for example those described in T. W. Greene, P. G. M. Wuts in "Protective Groups in Organic Synthesis", Wiley, 1991 and 1999, and the protective groups of which may be cleaved by methods known from the literature, in the course of the synthesis sequence, to form compounds of formula (I), are known from the literature, or their synthesis is described in the Examples, or they may be prepared for example using methods of synthesis known in the literature or analogously to methods of synthesis known in the literature as described for example in WO2007/003536, DE4429079, U.S. Pat. No. 4,490,369, DE3515864, U.S. Pat. No. 5,175,157, DE1921861, WO85/00808 or in G. Bobowski et al., J. Heterocyclic Chem. 16, 1525, 1979 or in P. D. Johnson et al., Bioorg. Med. Chem. Lett 2003, 4197.

For example, a compound of general formula (IV) wherein $R^3$ denotes a hydrogen atom and A1, A2, A3, K1, K2, K3, K4 and X are defined as in embodiment 1 may be prepared by reduction of the nitro group of a compound of general formula (X)

(X)

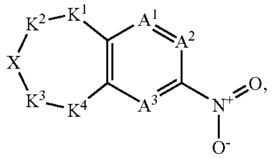

wherein A1, A2, A3, K1, K2, K3, K4 and X are defined as in embodiment 1, as follows.

The reduction of the nitro group is conveniently carried out for example in a solvent or mixture of solvents such as water, aqueous ammonium chloride solution, hydrochloric acid, sulphuric acid, phosphoric acid, formic acid, acetic acid, acetic anhydride with metals such as iron, zinc, tin or sulphur compounds such as ammonium sulphide, sodium sulphide or sodium dithionite or by catalytic hydrogenation with hydrogen, for example under a pressure between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminum hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethylether, diethyleneglycoldimethylether, dioxane, tetrahydrofuran, N-methylpyrrolidinone, or N-ethyl-diisopropylamine, N-$C_{1-5}$-alkylmorpholine, N-$C_{1-5}$-alkylpiperidine, N-$C_{1-5}$-alkylpyrrolidine, triethylamine, pyridine, for example at temperatures between −30 and 250° C., but preferably between 0 and 150° C.

(c) The components of general formula (V)

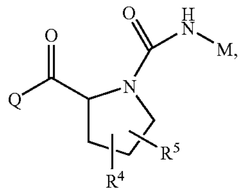

(VI)

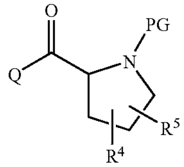

(VIII)

O═C═N-M (IX)

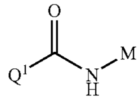

wherein $R^4$, $R^5$, $R^6$ and $R^2$ are defined as in embodiment 1, and wherein Q/$Q^1$ denotes for example a hydroxy or $C_{1-4}$-alkyloxy group, a halogen atom, an alkyloxycarbonyloxy or acyloxy group which may optionally be protected at any amino, hydroxy, carboxy or thiol groups present by common protective groups such as for example those described in T. W. Greene, P. G. M. Wuts in "Protective Groups in Organic Synthesis", Wiley, 1991 and 1999, and the protective groups of which may be cleaved by methods known from the literature, in the course of the synthesis sequence, to form compounds of formula (I), are known from the literature, or their synthesis is described in the Examples, or they may be prepared for example using methods of synthesis known in the literature or analogously to methods of synthesis known in the literature as described for example in WO2005/92849, WO2004/87646 or WO2003/45912.

In the reactions described above any reactive groups present such as hydroxy, carboxy, amino, alkylamino or imino groups may be protected during the reaction by conventional protecting groups which are cleaved again after the reaction.

For example, a suitable protecting group for a hydroxy group may be the methoxy, benzyloxy, trimethylsilyl, acetyl, benzoyl, tert.butyl, trityl, benzyl or tetrahydropyranyl group.

Suitable protecting groups for a carboxyl group might be the trimethylsilyl, methyl, ethyl, tert.butyl, benzyl or tetrahydropyranyl group.

Suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

Suitable protecting groups for an ethynyl group might be the trimethylsilyl, diphenylmethylsilyl, tert.butyldimethylsilyl or a 1-hydroxy-1-methyl-ethyl group.

Other protective groups which may be used and their cleaving are described in T. W. Greene, P. G. M. Wuts, "Protective Groups in Organic Synthesis", Wiley, 1991 and 1999.

Any protective group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A methoxy group is expediently cleaved in the presence of boron tribromide in a solvent such as methylene chloride at temperatures between −35 and −25° C.

A 2,4-dimethoxybenzyl group is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

Moreover the compounds of general formula (I) obtained may be resolved into their enantiomers and/or diastereomers.

Thus, for example, the compounds of general formula I obtained which occur as racemates may be separated by methods known per se (cf. Allinger N. L. And Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatographic column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula I may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I as well as the tautomers, the enantiomers, the diastereomers and the physiologically acceptable salts thereof have valuable pharmacological properties, particularly an antithrombotic activity, which is preferably based on an effect on thrombin or factor Xa, for example on a thrombin-inhibiting or factor Xa-inhibiting activity, on a prolonging effect on the aPTT time and on an inhibiting effect on related serine proteases such as e.g. urokinase, factor VIIa, factor IX, factor XI and factor XII.

The compounds listed in the experimental section may be investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free.

Factor Xa (Calbiochem), spec. Activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 μMol/l Procedure:

10 μl of a 23.5-times concentrated starting solution of the test substance or solvent (control), 175 μl of TRIS/HSA buffer and 25 μl of a 65.8 U/L Factor Xa working solution are incubated for 10 minutes at 37° C. After the addition of 25 μl of S 2765 working solution (2.82 mMol/l) the sample is measured in a photometer (SpectraMax 250) at 405 nm for 600 seconds at 37° C.

Evaluation:

1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 μmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, thrombophlebitis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbation of COPD, for treating ulcerative colitis, for treating and preventing coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

The compounds specified may also be used as anticoagulants in connection with the preparation, storage, fractionation or use of whole blood or in invasive therapies, e.g. for coating prostheses, artificial heart valves and catheters for reducing the risk of thrombosis.

In view of their pharmacological properties the new compounds and the physiologically acceptable salts thereof are also suitable for treating Alzheimer's and Parkinson's disease. One rationale for this can be seen for example in the following findings, from which it can be concluded that thrombin inhibitors or factor Xa inhibitors, by inhibiting thrombin formation or activity, could be valuable drugs for treating Alzheimer's and Parkinson's disease. Clinical and experimental studies indicate that neurotoxic mechanisms, for example the inflammation that accompanies the activation of proteases of the clotting cascade, are involved in the dying off of neurones following brain damage. Various studies indicate an involvement of thrombin in neurodegenerative processes, e.g. following a stroke, repeated bypass operations or traumatic brain injury. An increased thrombin activity was able to be detected for example some days after peripoheral nerve damage. It was also shown that thrombin causes neurite retraction and glia proliferation, and apoptosis in primary cultures of neurones and neuroblastoma cells (for an overview see: *Neurobiol. Aging,* 2004, 25(6), 783-793). In addition, various in vitro studies on the brains of patients with Alzheimer's disease indicate that thrombin plays a part in the pathogenesis of this disease (*Neurosci. Lett.,* 1992, 146, 152-54). An accumulation of immunoreactive thrombin has been detected in neurite plaques in the brains of Alzheimer's patients. It was demonstrated in vitro that thrombin also plays a part in the regulation and stimulation of the production of Amyloid Precursor Protein (APP) as well as in the cleaving of APP into fragments which can be detected in the amyloid plaques in the brains of Alzheimer's patients. It has also been shown that thrombin-induced microglial activation in vivo leads to the degeneration of nigral dopaminergic neurones. These findings lead one to conclude that microglial activation, triggered by endogenous substance(s) such as thrombin, for example, are involved in the neuropathological process of the cell death of dopaminergic neurones, such as occurs in patients with Parkinson's disease (*J. Neurosci.,* 2003, 23, 5877-86).

The new compounds and the physiologically acceptable salts thereof can also be used for the prevention and treatment of arterial vascular diseases in combination therapy with lipid-lowering active substances such as HMG-CoA reductase inhibitors and vasodilators, particularly ACE inhibitors, angiotensin II antagonists, renin inhibitors, β-receptor antagonists, α-receptor antagonists, diuretics, Ca-channel blockers, or stimulators of soluble guanylate cyclase.

By increasing the antithrombotic activity the new compounds and the physiologically acceptable salts thereof can also be used in combination therapy with other anticoagulants such as, for example, unfractionated heparin, low-molecular heparin, fondaparinux or direct thrombin inhibitors, for example recombinant hirudine or "active-site" thrombin inhibitors.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, prasugrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

EXPERIMENTAL SECTION

The following Examples are intended to illustrate the invention, without restricting its scope.

As a rule, melting points and/or IR, UV, $^1$H-NMR and/or mass spectra have been obtained for the compounds prepared. Unless otherwise stated, $R_f$-values were obtained using ready-made silica gel 60 $F_{254}$ TLC plates (E. Merck, Darmstadt, Item no. 1.05714) without chamber saturation. The $R_f$-values obtained under the name Alox were determined using ready-made aluminium oxide 60 $F_{254}$ TLC plates (E. Merck, Darmstadt, Item no. 1.05713) without chamber saturation. The $R_f$-values obtained under the name Reversed-phase-8 (RP-8) were determined using ready-made RP-8 $F_{254s}$ TLC plates (E. Merck, Darmstadt, Item no. 1.15684) without chamber saturation. The ratios given for the eluants refer to units by volume of the solvents in question. Chromatographic purification was done using silica gel supplied by Messrs Millipore (MATREX™, 35-70 μm). If the configuration is not specified in detail, it is unclear whether the compound in question is a pure stereoisomer or a mixture of enantiomer and diastereomer.

The HPLC-MS data were obtained under the following conditions.

Waters Alliance 2690, Waters ZQ2000 Mass Spectrometer with diode array detector 996.

The mobile phase used was:

A: water with 0.10% TFA

B: acetonitrile with 0.8% TFA

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |
| 4.50 | 2 | 98 | 1.00 |
| 5.00 | 95 | 5 | 1.00 |

The stationary phase used was an X-Terra MS C18 column, 2.5 μm, 4.6 mm×30 mm.

The diode array detection was carried out in a wavelength range of 210-500 nm.

The following abbreviations are used in the test descriptions.

| | |
|---|---|
| DCM | dichloromethane |
| DIPEA | N-ethyl-diisopropylamine |
| DMF | N,N-dimethylformamide |
| EtOH | ethanol |
| sat. | saturated |
| h | hour(s) |
| HATU | O-(7-azabenzotriazol-1-yl)-N,N,N',N'-tetramethyluronium-hexafluorophosphate |
| i. vac. | in vacuo |
| conc. | concentrated |
| min | minute(s) |
| NMM | N-methyl-morpholine |
| $R_f$ | retention factor |
| $R_t$ | retention time |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |

Example 1

(2R,4R)-4-methoxy-pyrrolidine-1,2-dicarboxylic acid-1-(4-chloro-phenyl)amide-2-(3-methyl-2,3,4,5-tetrahydro-1H-benzo[d]azepin-7-yl)amide

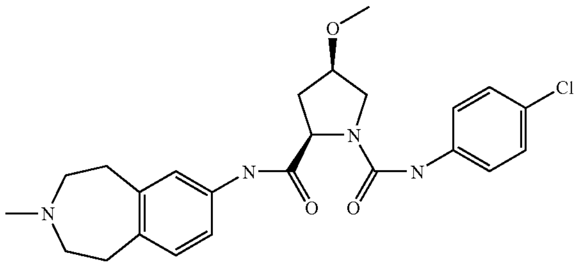

(a) 1-tert.butoxy (2R,4R)-4-methoxy-pyrrolidine-1,2-dicarboxylate 2-(3-methyl-2,3,4,5-tetrahydro-1H-benzo[d]azepin-7-yl)-amide 0.170 g (0.693 mmol) 1-tert.butoxy (2R,4R)-4-methoxy-pyrrolidine-1,2-dicarboxylate are dissolved in 5.0 ml THF, combined with 0.19 ml (1.7 mmol) NMM and 0.234 g (0.728 mmol) TBTU and stirred for 15 min. Then 0.122 g (0.693 mmol) 7-amino-3-methyl-2,3,4,5-tetrahydro-1H-benzo[d]azepine are added and the mixture is stirred for 16 h. The reaction mixture is concentrated i. vac., combined with 20 ml of ethyl acetate and washed successively with sat. $NaHCO_3$ solution, sat. NaCl solution and water and then with $Na_2SO_4$ and evaporated to dryness i. vac.

Yield: 0.210 g (75%)

$R_f$-value: 0.8 (silica gel; dichloromethane/ethanol/ammonia=80:20:2)

$C_{22}H_{33}N_3O_4$ (403.515)

Mass spectrum: $(M+H)^+=404$

(b) (2R,4R)-4-methoxy-pyrrolidine-2-carboxylic acid-(3-methyl-2,3,4,5-tetrahydro-1H-benzo[d]azepin-7-yl)-amide 1.5 ml of 6 M HCl are added to a solution of 0.210 g (0.520 mmol) 1-tert.butoxy (2R,4R)-4-methoxy-pyrrolidine-1,2-dicarboxylate 2-(3-methyl-2,3,4,5-tetrahydro-1H-benzo[d]azepin-7-yl)-amide in 2.0 ml THF over 2 h and the mixture is stirred for a total of 18 h. The reaction mixture is evaporated down i. vac., combined with methanol several times and evaporated down again.

Crude yield: 0.230 g (quantitative)

$R_f$-value: 0.25 (silica gel; dichloromethane/ethanol/ammonia=80:20:2)

$C_{17}H_{25}N_3O_2$ (303.515)x2HCl

Mass spectrum: $(M+H)^+=304$

(c) (2R,4R)-4-methoxy-pyrrolidine-1,2-dicarboxylic acid-1-(4-chlorophenyl)amide-2-(3-methyl-2,3,4,5-tetrahydro-1H-benzo[d]azepin-7-yl)amide 40.8 mg (0.266 mmol) 4-chlorophenylisocyanate are added to a solution of 0.100 g (0.266 mmol) (2R,4R)-4-methoxy-pyrrolidine-2-carboxylic acid-(3-methyl-2,3,4,5-tetrahydro-1H-benzo[d]azepin-7-yl)-amide in 2.0 ml dioxane and 2.0 ml DMF and the mixture is stirred for 18 h. The reaction mixture is concentrated i. vac. and purified by prep. HPLC (method A)

Yield: 15 mg (11%)

$R_f$-value: 0.4 (silica gel; dichloromethane/ethanol/ammonia=80:20:2)

$C_{24}H_{29}ClN_4O_3$ (456.974)xHCOOH

Mass spectrum: $(M+H)^+=457/459$ (chlorine isotopes)

The following compounds may be prepared analogously:

| Ex. | Structural formula | Yield | Mass peak(s) | DC/HPLC |
|---|---|---|---|---|
| 2 | 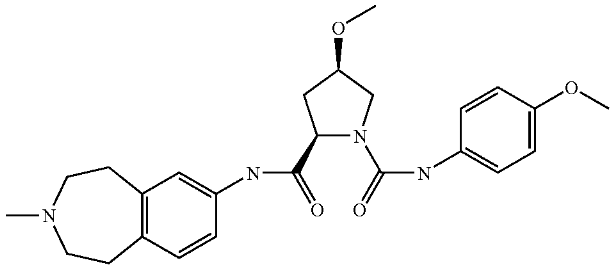 (2R,4R)-4-methoxy-pyrrolidine-1,2-dicarboxylic acid-1-(4-methoxy-phenyl)amide-2-(3-methyl-2,3,4,5-tetrahydro-1H-benzo[d]azepin-7-yl)amide | 75% | $(M + H)^+ = 453$ | $R_f$-value: 0.4 (silica gel; DCM/EtOH/NH3 = 80:20:2) |
| 3 | 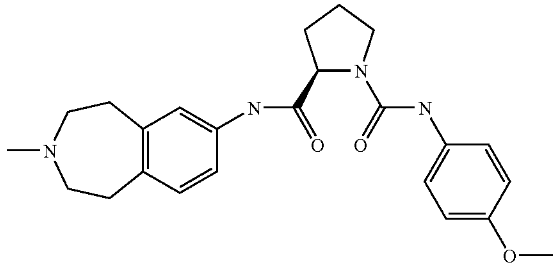 (2R)-pyrrolidine-1,2-dicarboxylic acid-1-(4-methoxy-phenyl)amide-2-(3-methyl-2,3,4,5-tetrahydro-1H-benzo[d]azepin-7-yl)amide | 10% | $(M + H)^+ = 423$ $(M - H)^- = 421$ | $R_f$-value: 0.56 (RP-8; MeOH/5% NaCl-soln. = 6:4) |

-continued

| Ex. | Structural formula | Yield | Mass peak(s) | DC/HPLC |
|---|---|---|---|---|
| 4 | 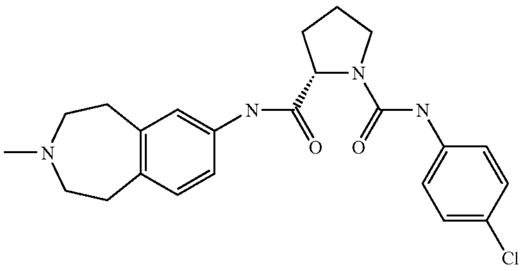 | 6% | $(M + H)^+$ = 427/429 (chlorine isotopes) | $R_f$-value: 0.44 (RP-8; MeOH/5% NaCl-soln. = 6:4) |
| | (2S)-pyrrolidine-1,2-dicarboxylic acid-1-(4-chloro-phenyl)amide-2-(3-methyl-2,3,4,5-tetrahydro-1H-benzo[d]azepin-7-yl)amide | | | |
| 5 | 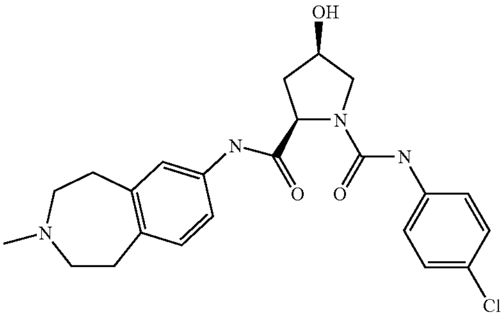 | 30% | $(M + H)^+$ = 443/445 (chlorine isotopes) | $R_t$-time: 2.27 min (method A) |
| | (2R,4R)-4-hydroxy-pyrrolidine-1,2-dicarboxylic acid-1-(4-chloro-phenyl]amide-2-(3-methyl-2,3,4,5-tetrahydro-1H-benzo[d]azepin-7-yl)amide | | | |
| 6 | 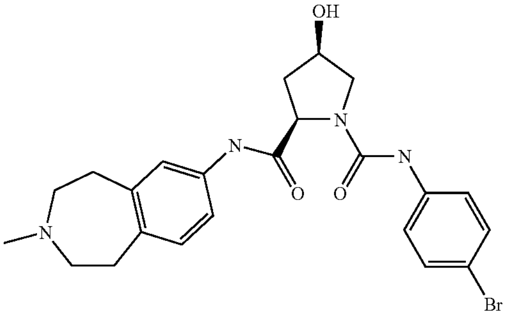 | 21% | $(M + H)^+$= 487/489 (bromine isotopes) | $R_t$ -time: 2.28 min (method A) |
| | (2R,4R)-4-hydroxy-pyrrolidine-1,2-dicarboxylic acid-1-(4-bromo-phenyl)amide-2-(3-methyl-2,3,4,5-tetrahydro-1H-benzo[d]azepin-7-yl)amide | | | |
| 7 | 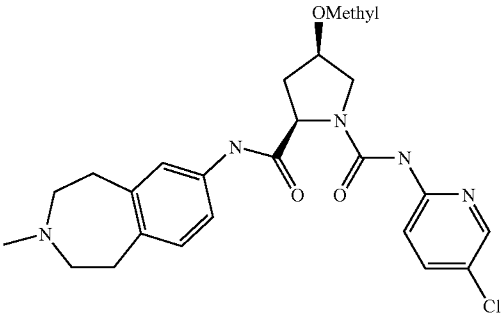 | 65% | $(M + H)^+$ = 458/460 (chlorine isotopes) | $R_f$-value: 0.3 (silica gel; DCM/EtOH/NH3 = 80:20:2) |
| | (2R,4R)-4-methoxy-pyrrolidine-1,2-dicarboxylic acid-1-(5-chloro-pyridin-2-yl)amide-2-(3-methyl-2,3,4,5-tetrahydro-1H-benzo[d]azepin-7-yl)amide | | | |

-continued

| Ex. | Structural formula | Yield | Mass peak(s) | DC/HPLC |
|---|---|---|---|---|
| 8 | 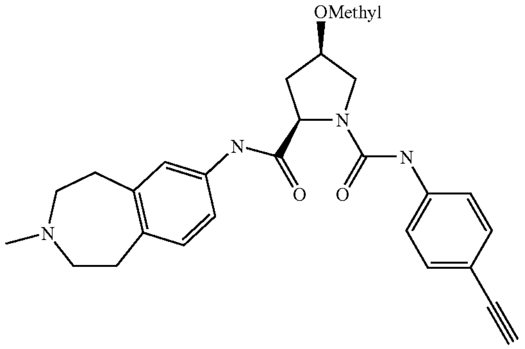 (2R,4R)-4-methoxy-pyrrolidine-1,2-dicarboxylic acid-1-(4-ethynyl-phenyl)amide-2-(3-methyl-2,3,4,5-tetrahydro-1H-benzo[d]azepin-7-yl)-amide | 38% | $(M + H)^+ = 447$ | $R_f$-value: 0.7 (silica gel; DCM/EtOH/NH3 = 80:20:2) |
| 9 | 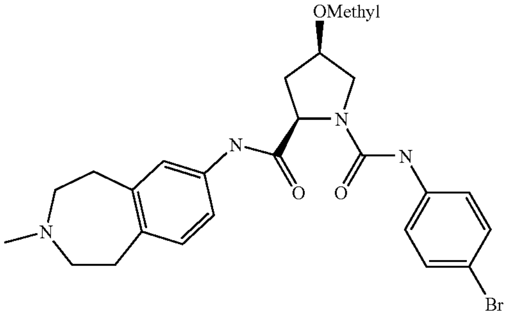 (2R,4R)-4-methoxy-pyrrolidine-1,2-dicarboxylic acid-1-(4-bromo-phenyl)amide-2-(3-methyl-2,3,4,5-tetrahydro-1H-benzo[d]azepin-7-yl)amide | 62% | $(M + H)^+$ = 501/503 (bromine isotopes) | $R_t$-time: 4.17 min (method A) |
| 10 | 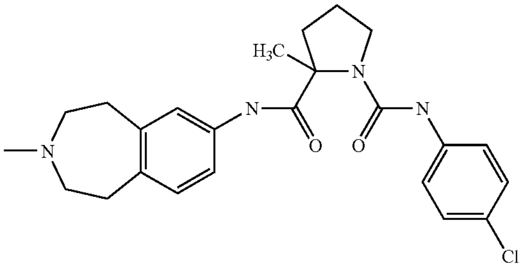 pyrrolidin-2-methyl-1,2-dicarboxylic acid-1-(4-chloro-phenyl)amide-2-(3-methyl-2,3,4,5-tetrahydro-1H-benzo[d]azepin-7-yl)amide | 80% | $(M + H)^+$ = 441/443 (chlorine isotopes) | $R_f$-value: 0.6 (silica gel; DCM/EtOH/NH3 = 80:20:2) |

Example 11

2,5-dihydro-pyrrole-1,2-dicarboxylic acid-1-(4-chloro-phenyl)amide-2-[(3-methyl-2,3,4,5-tetrahydro-1H-benzo[d]azepin-7-yl)amide

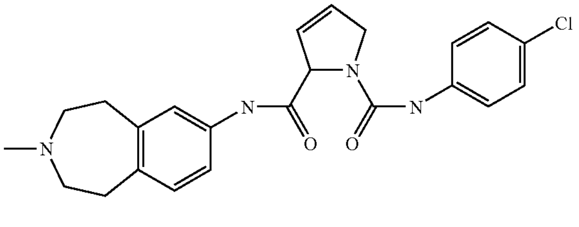

(a) 1-(4-chloro-phenylcarbamoyl)-2,5-dihydro-1H-pyrrole-2-carboxylic acid 0.250 g (2.21 mmol) 3,4-dehydro-DL-proline are dissolved in 15 ml of 5% $NaHCO_3$ solution, combined with 0.678 ml (4.42 mmol) 4-chlorophenylisocyanate and stirred for 16 h at 80° C. Then the mixture is cooled, filtered and the residue is washed with water. The filtrate is adjusted to pH 1 with semi-concentrated HCl, extracted 2× with ethyl acetate, dried on sodium sulphate and concentrated i. vac.

Yield: 0.640 g (quantitative, slightly impure)

$C_{12}H_{11}N_2O_3$ (266.680).

Mass spectrum: $(M+H)^+$=265/267 chlorine isotopes (b) 2,5-dihydro-pyrrole-1,2-dicarboxylic acid-1-(4-chloro-phenyl)amide-2-(3-methyl-2,3,4,5-tetrahydro-1H-benzo[d]azepin-7-yl)amide 0.200 g (0.750 mmol) 1-(4-chloro-phenylcarbamoyl)-2,5-dihydro-1H-pyrrole-2-carboxylic acid are reacted analogously to Example 1a with 0.132 g (0.750 mmol) of 7-amino-3-methyl-2,3,4,5-tetrahydro-1H-benzo[d]azepine, NMM and TBTU to obtain the title compound.

Yield: 50 mg (14%)

$R_f$ value: 0.6 (silica gel; dichloromethane/ethanol/ammonia=80:20:2)

$C_{23}H_{25}ClN_4O_2$ (424.923)

Mass spectrum: $(M+H)^+$=425/427 (chlorine isotopes)

The following compound may be prepared analogously:

| Ex. | Structural formula | Mass peak(s) | DC/HPLC |
|---|---|---|---|
| 12 | 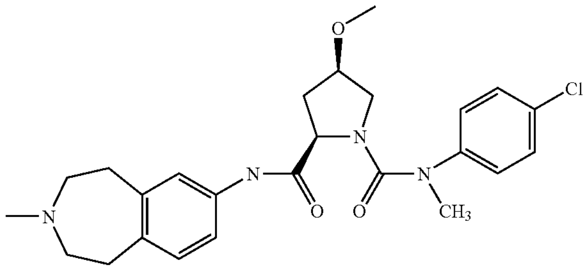 | $(M + H)^+$ = 471/473 (chlorine isotopes) | Rf value: 0.3 (silica gel; dichloromethane/ethanol/ammonia = 80:20:2) |
| | (2R,4R)-4-methoxy-pyrrolidine-1,2-dicarboxylic acid-1-N-(4-chloro-phenyl)-N-methyl-amide-2-(3-methyl-2,3,4,5-tetrahydro-1H-benzo[d]azepin-7-yl)amide | | |

Example 13

(2R,4R)-4-methoxy-pyrrolidine-1,2-dicarboxylic acid-1-(4-chloro-phenyl)amide-2-((R)-1,3-dimethyl-2,3,4,5-tetrahydro-1H-benzo[d]azepin-8-yl)amide and (2R,4R)-4-methoxy-pyrrolidine-1,2-dicarboxylic acid-1-(4-chloro-phenyl)amide-2-((S)-1,3-dimethyl-2,3,4,5-tetrahydro-1H-benzo[d]azepin-8-yl)amide

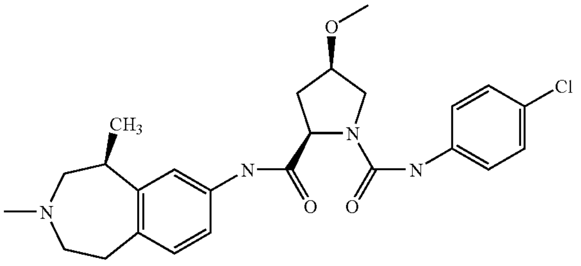

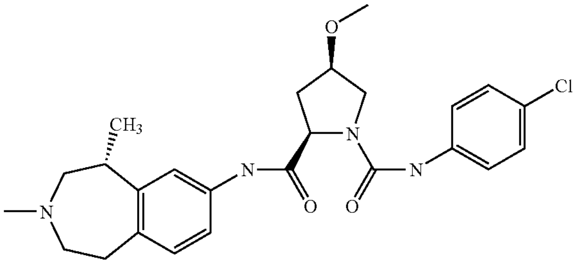

(a) 1-methyl-2-oxo-2,3,4,5-tetrahydro-1H-benzo[d]azepine 8.0 g (37 mmol) 2-chloro-N-(2-phenylethyl)-propanamide and 15 g (112 mmol) aluminium trichloride are carefully mixed at 90° C. and heated to 150° C. for 6 h. The mixture is diluted with water and methanol and extracted with EtOAc. The combined organic phases are dried with $Na_2SO_4$, concentrated i. vac. and purified by chromatography.

(b) 1-methyl-2,3,4,5-tetrahydro-1H-benzo[d][azepine 2.7 g (15 mmol) 1-methyl-2-oxo-2,3,4,5-tetrahydro-1H-benzo[d]azepine is added to 46 ml of 1 M $BH_3$-THF complex solution and stirred for 16 h at ambient temperature. 50 ml of methanol are carefully added, followed by 30 ml of 2M HCl. The mixture is extracted with EtOAc, the combined organic phases are dried with $Na_2SO_4$, concentrated i. vac. and purified by chromatography.

(c) 1,3-dimethyl-2,3,4,5-tetrahydro-1H-benzo[d]azepine 2.5 g (12 mmol) 1-methyl-2,3,4,5-tetrahydro-1H-benzo[d][azepine in 4.5 ml formic acid are combined with 3.6 ml formalin solution in water (37%) with stirring at ambient temperature and stirred for 3 h at 70° C. The reaction mixture is made alkaline with NaOH solution (50%) while cooling with an ice bath and extracted with tert.-butylmethylether. The organic phase is dried on sodium sulphate and evaporated to dryness i. vac.

d) 1,3-dimethyl-7-nitro-2,3,4,5-tetrahydro-1H-benzo[d]azepine and 1,3-dimethyl-8-nitro-2,3,4,5-tetrahydro-1H-benzo[d]azepine 1.79 g (10 mmol) of 1,3-dimethyl-2,3,4,5-tetrahydro-1H-benzo[d]azepine is mixed with 3.7 ml conc. $H_2SO_4$ and 0.71 ml of 65% $HNO_3$ at −5° C. and stirred for 1 h at −5° C. to 0° C. The mixture is added to 100 ml ice water and 10 ml NaOH are added thereto. The mixture is extracted with EtOAc, the combined organic phases are dried with $Na_2SO_4$, concentrated and purified by chromatography (eluant: dichloromethane:95% ethanol/5% ammonia 99:1 to 95:5). A mixture of the title compounds is obtained.

(d) 1,3-dimethyl-7-amino-2,3,4,5-tetrahydro-1H-benzo[d]azepine and 1,3-dimethyl-8-amino-2,3,4,5-tetrahydro-1H-benzo[d]azepine 1.4 g (6.3 mmol) of a mixture of 1,3-dimethyl-7-nitro-2,3,4,5-tetrahydro-1H-benzo[d]azepine and 1,3-dimethyl-8-nitro-2,3,4,5-tetrahydro-1H-benzo[d]azepine, 20 ml of methanol and 0.20 g 10% palladium on charcoal is hydrogenated for 5.5 h under a hydrogen atmosphere (50 psi). It is filtered, concentrated and the mixture is purified by chromatography with silica gel (eluant: dichloromethane:95% ethanol/5% ammonia 99:1 to 80:20). 0.45 g of 1,3-dimethyl-7-amino-2,3,4,5-tetrahydro-1H-benzo[d]azepine are obtained $R_f$ value: 0.75 (silica gel; dichloromethane/ethanol/ammonia=80:20:2)

$C_{12}H_{18}N_2$ (190.28)

Mass spectrum: $(M+H)^+$=191 and 0.55 g of 1,3-dimethyl-8-amino-2,3,4,5-tetrahydro-1H-benzo[d]azepine.

$R_f$ value: 0.70 (silica gel; dichloromethane/ethanol/ammonia=80:20:2)

$C_{12}H_{18}N_2$ (190.28)

Mass spectrum: $(M+H)^+$=191.

(e) (2R,4R)-4-methoxy-pyrrolidine-1,2-dicarboxylic acid-1-(4-chlorophenyl)amide-2-((R)-1,3-dimethyl-2,3,4,5-tetrahydro-1H-benzo[d]azepin-8-yl)amide and (2R,4R)-4-methoxy-pyrrolidine-1,2-dicarboxylic acid-1-(4-chlorophenyl)amide-2-((S)-1,3-dimethyl-2,3,4,5-tetrahydro-1H-benzo[d]azepin-8-yl)amide A mixture of 5.0 ml DMF, 0.157 g (0.53 mmol) (2R,4R)-1-(4-chlorophenylcarbamoyl)-4-methoxy-pyrrolidine-2-carboxylic acid, 0.20 ml of NMM, 0.21 g (0.55 mmol) of HATU and 0.10 g (0.53 mmol) of 1,3-dimethyl-8-amino-2,3,4,5-tetrahydro-1H-benzo[d]azepine are heated to 70° C. overnight. The reaction mixture is concentrated, taken up in EtOAc and washed with sat. $NaHCO_3$ solution and water and sat. NaCl solution. The organic phase is dried with $NaSO_4$, evaporated down and purified by HPLC-MS. A mixture of the two diastereomers is obtained.

$R_f$ value: 0.8 (silica gel; dichloromethane/ethanol/ammonia=80:20:2)

$C_{25}H_{31}ClN_4O_3$ (470.99)

Mass spectrum: $(M+H)^+$=471/473 (chlorine isotopes)

Example 14

(2R,4R)-4-methoxy-pyrrolidine-1,2-dicarboxylic acid-1-(4-chloro-phenyl)amide-2-((R)-1,3-dimethyl-2,3,4,5-tetrahydro-1H-benzo[d]azepin-7-yl)amide and (2R,4R)-4-methoxy-pyrrolidine-1,2-dicarboxylic acid-1-(4-chloro-phenyl)amide-2-((S)-1,3-dimethyl-2,3,4,5-tetrahydro-1H-benzo[d]azepin-7-yl)amide

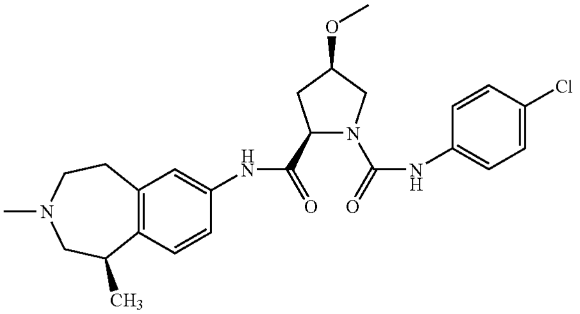

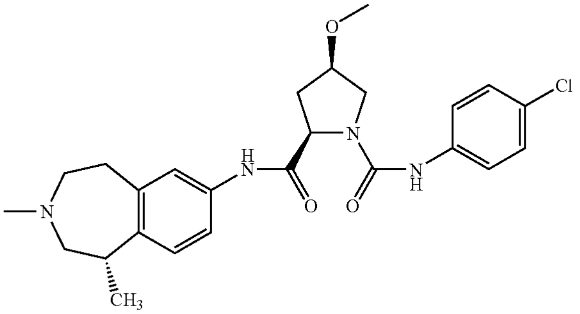

A mixture of the two title compounds was prepared analogously to Example 13e from (2R,4R)-1-(4-chloro-phenylcarbamoyl)-4-methoxy-pyrrolidine-2-carboxylic acid and 1,3-dimethyl-7-amino-2,3,4,5-tetrahydro-1H-benzo[d]azepine.

$R_f$ value: 0.8 (silica gel; dichloromethane/ethanol/ammonia=80:20:2)

$C_{25}H_{31}ClN_4O_3$ (470.99)

Mass spectrum: $(M+H)^+$=471/473 (chlorine isotopes)

The following compounds may be prepared analogously to the methods described above or methods known from the literature as described for example in WO2007/3536, WO2004/87646 or WO2005/92849:

| Ex. | Structural formula | Mass peak(s) | DC/HPLC |
|---|---|---|---|
| 15 | 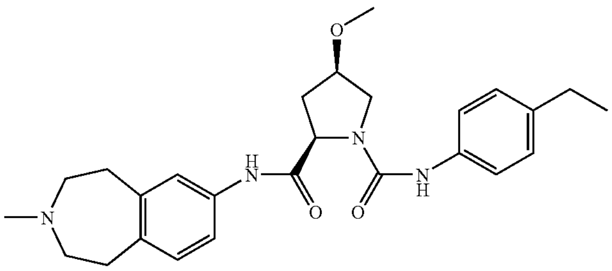<br>(2R,4R)-4-methoxy-pyrrolidine-1,2-dicarboxylic acid-1-N-(4-ethyl-phenyl)amide-2-(3-methyl-2,3,4,5-tetrahydro-1H-benzo[d]azepin-7-yl)-amide | $(M + H)^+$ = 451 | |

-continued

| Ex. | Structural formula | Mass peak(s) | DC/HPLC |
|---|---|---|---|
| 16 | 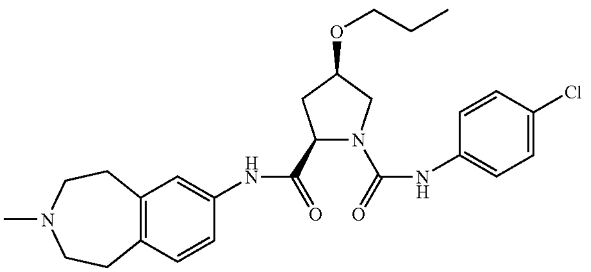<br>(2R,4R)-4-propyloxy-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 485/487 chlorine isotopes | |
| 17 | 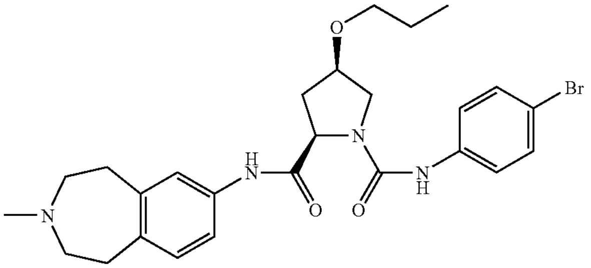<br>(2R,4R)-4-propyloxy-pyrrolidine-1,2-dicarboxylic acid-1-N-(4-bromo-phenyl)amide-2-(3-methyl-2,3,4,5-tetrahydro-1H-benzo[d]azepin-7-yl)-amide | $(M + H)^+$ = 529/531 bromine isotopes | |
| 18 | 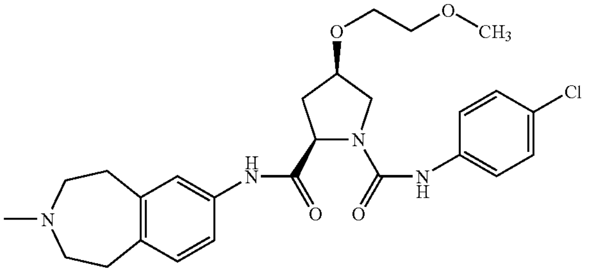<br>(2R)-4-methoxyethoxy-pyrrolidine-1,2-dicarboxylic acid-1-N-(4-chloro-phenyl)amide-2-(3-methyl-2,3,4,5-tetrahydro-1H-benzo[d]azepin-7-yl)-amide-mixture of stereoisomers | $(M + H)^+$ = 501/503 chlorine isotopes | $R_f$-value: 0.8 (silica gel; dichloromethane/ethanol/ammonia = 80:20:2) |
| 19 | 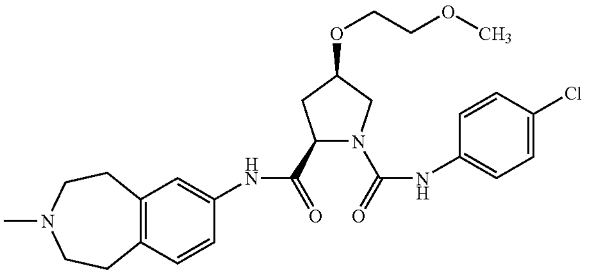<br>(2R,4R)-4-methoxyethoxy-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 501/503 chlorine isotopes | $R_f$-value: 0.8 (silica gel; dichloromethane/ethanol/-ammonia = 80:20:2) |
| 20 | 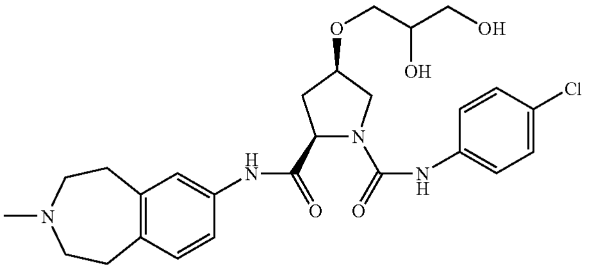<br>(2R,4R)-4-(2,3-dihydroxy)propyl-1,2-dicarboxylic acid-1-N-(4-chloro-phenyl)amide-2-(3-methyl-2,3,4,5-tetrahydro-1H-benzo[d]azepin-7-yl)-amide-mixture of stereoisomers | $(M + H)^+$ = 517/519 chlorine isotopes | |

-continued

| Ex. | Structural formula | Mass peak(s) | DC/HPLC |
|---|---|---|---|
| 21 | 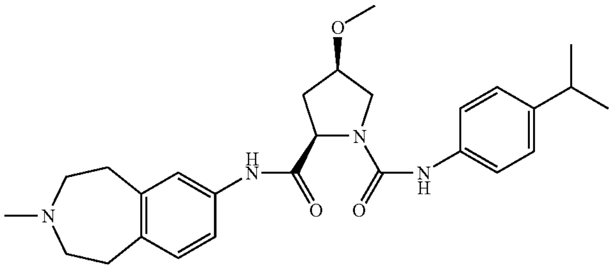<br>(2R,4R)-4-methoxy-pyrrolidine-1,2-dicarboxylic acid-1-N-(4-isopropyl-phenyl)amide-2-(3-methyl-2,3,4,5-tetrahydro-1H-benzo[d]azepin-7-yl)-amide | $(M + H)^+ = 465$ | |
| 22 | 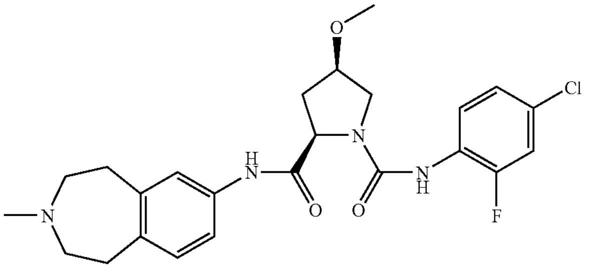<br>(2R,4R)-4-methoxy-pyrrolidine-1,2-dicarboxylic acid-1-N-(4-chloro-2-fluoro-phenyl)-amide-2-(3-methyl-2,3,4,5-tetrahydro-1H-benzo[d]azepin-7-yl)-amide | $(M + H)^+ =$ 475/477 chlorine isotopes | |
| 23 | 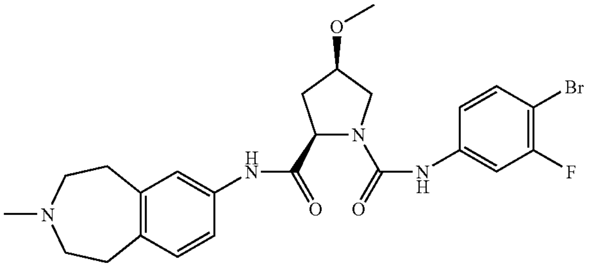<br>(2R,4R)-4-methoxy-pyrrolidine-1,2-dicarboxylic acid-1-N-(4-bromo-3-fluoro-phenyl)amide-2-(3-methyl-2,3,4,5-tetrahydro-1H-benzo[d]azepin-7-yl)-amide | $(M + H)^+ =$ 519/521 bromine isotopes | |
| 24 | 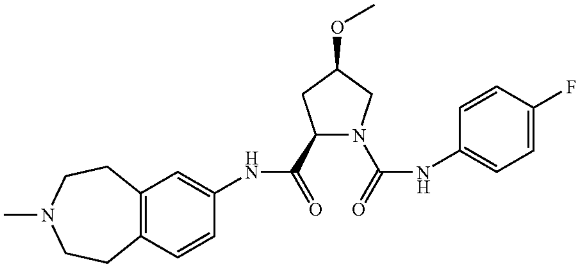<br>(2R,4R)-4-methoxy-pyrrolidine-1,2-dicarboxylic acid-1-N-(4-fluoro-phenyl)amide-2-(3-methyl-2,3,4,5-tetrahydro-1H-benzo[d]azepin-7-yl)-amide | $(M + H)^+ = 441$ | $R_f$-value: 0.87 (silica gel; dichloromethane/ethanol/-ammonia = 80:20:2) |
| 25 | 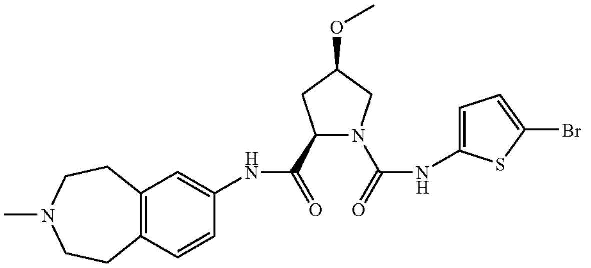<br>(2R,4R)-4-methoxy-pyrrolidine-1,2-dicarboxylic acid-1-N-(5-bromo-thien-2-yl)amide-2-(3-methyl-2,3,4,5-tetrahydro-1H-benzo[d]azepin-7-yl)-amide | $(M + H)^+ =$ 507/509 bromine isotopes | |

-continued

| Ex. | Structural formula | Mass peak(s) | DC/HPLC |
| --- | --- | --- | --- |
| 26 | 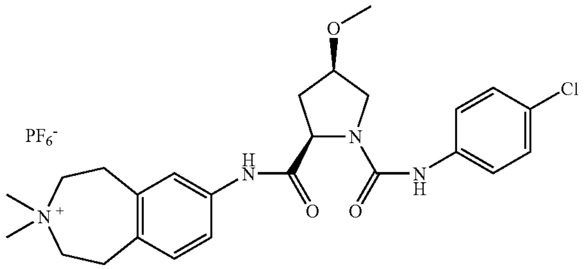 (2R,4R)-4-methoxy-pyrrolidine-1,2-dicarboxylic acid-1-N-(4-chloro-phenyl)amide-2-(3.3-dimethyl-2,3,4,5-tetrahydro-1H-benzo[d]azepin-7-ylium)-amide hexafluorophosphate | $(M + H)^+$ = 471/473 chlorine isotopes | |
| 27 | 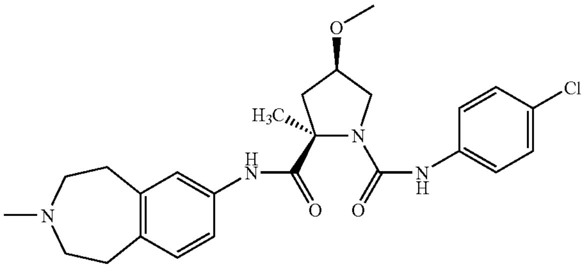 (2R,4R)-4-methoxy-2-methyl-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 471/473 chlorine isotopes | |
| 28 | 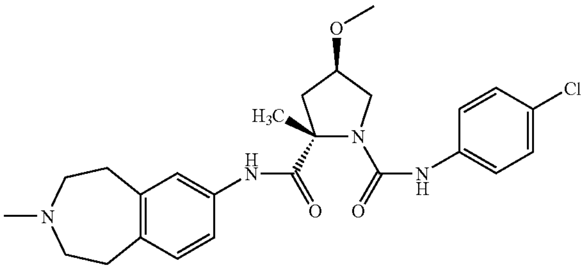 (2S,4R)-4-methoxy-2-methyl-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 471/473 chlorine isotopes | |
| 29 | 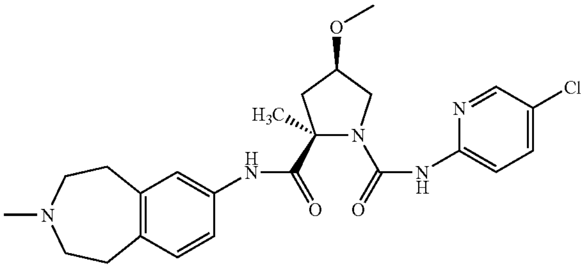 (2S,4R)-4-methoxy-2-methyl-pyrrolidine-1,2-dicarboxylic acid-1-N-(5-chloro-pyridin-2-yl)amide-2-(3-methyl-2,3,4,5-tetrahydro-1H-benzo[d]azepin-7-yl)-amide | $(M + H)^+$ = 472/474 chlorine isotopes | |
| 30 | 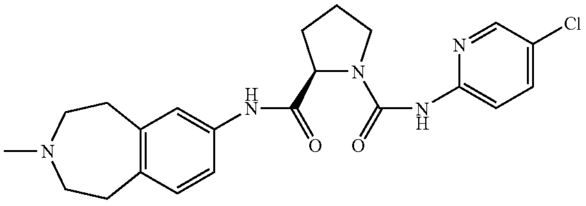 (2S)-pyrrolidine-1,2-dicarboxylic acid-1-N-(5-chloro-pyridin-2-yl)amide-2-(3-methyl-2,3,4,5-tetrahydro-1H-benzo[d]azepin-7-yl)-amide | $(M + H)^+$ = 428/430 chlorine isotopes | |

-continued

| Ex. | Structural formula | Mass peak(s) | DC/HPLC |
|---|---|---|---|
| 31 | 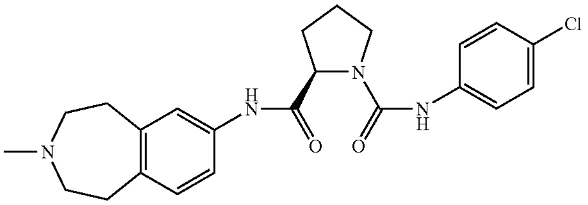<br>(2S)-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 427/429 chlorine isotopes | |
| 32 | 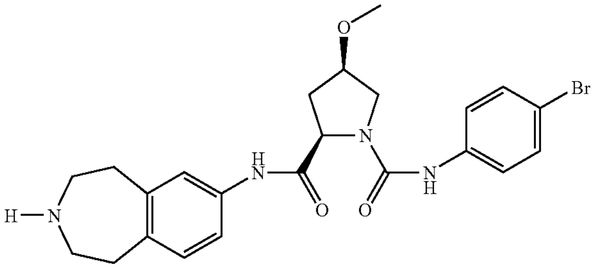<br>(2R,4R)-4-methyloxy-pyrrolidine-1,2-dicarboxylic acid-1-N-(4-bromo-phenyl)amide-2-(2,3,4,5-tetrahydro-1H-benzo[d]azepin-7-yl)-amide | $(M + H)^+$ = 487/489 bromine isotopes | |
| 33 | 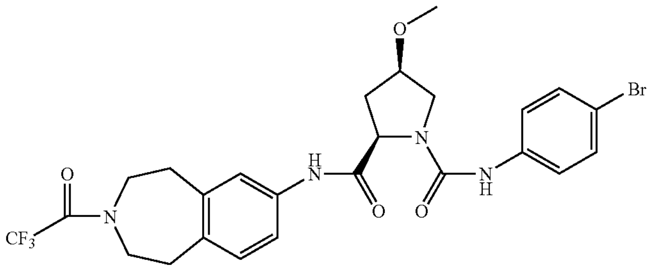<br>(2R,4R)-4-methyloxy-pyrrolidine-1,2-dicarboxylic acid-1-N-(4-bromo-phenyl)amide-2-(3-trifluoracetyl-2,3,4,5-tetrahydro-1H-benzo[d]azepin-7-yl)-amide | $(M - H)^-$ = 581/583 bromine isotopes | |
| 34 | 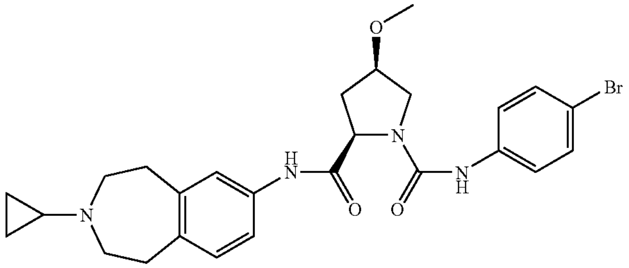<br>(2R,4R)-4-methyloxy-pyrrolidine-1,2-dicarboxylic acid-1-N-(4-bromo-phenyl)amide-2-(3-cyclopropyl-2,3,4,5-tetrahydro-1H-benzo[d]azepin-7-yl)-amide | $(M + H)^+$ = 527/529 bromine isotopes | $R_f$-value: 0.63 (RP-8; methanol/ 5% NaCl soln. = 6/4) |
| 35 | 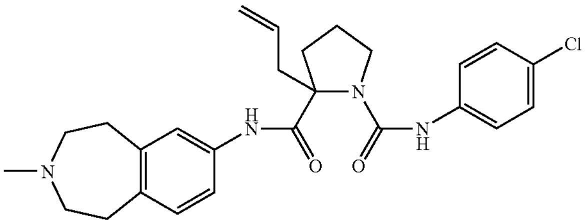<br>(rac)-2-allyl-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 467/469 chlorine isotopes | $R_f$-value: 0.41 (Alox; $CH_2Cl_2$/ethanol = 19/1) |

-continued

| Ex. | Structural formula | Mass peak(s) | DC/HPLC |
| --- | --- | --- | --- |
| 36 | 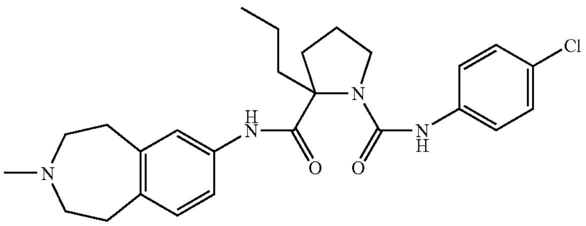 (rac)-2-propyl-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 469/471 chlorine isotopes | |
| 37 | 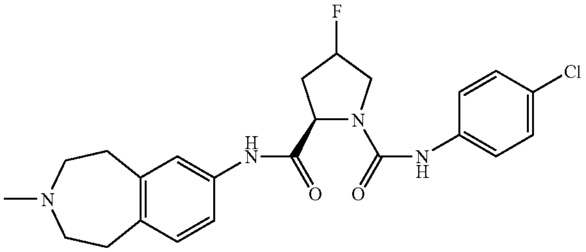 (2R)-4-fluoro-pyrrolidine-1,2-dicarboxylic acid-1-N-(4-chloro-phenyl)amide-2-(3-methyl-2,3,4,5-tetrahydro-1H-benzo[d]azepin-7-yl)-amide (stereoisomers) | $(M + H)^+$ = 445/447 chlorine isotopes | $R_f$-value: 0.7 (silica gel; dichloromethane/ethanol/ammonia = 80:20:2) |
| 38 | 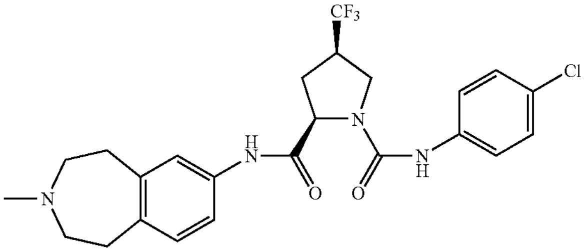 (2R,4R)-4-trifluoromethyl-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 495/497 chlorine isotopes | |
| 39 | 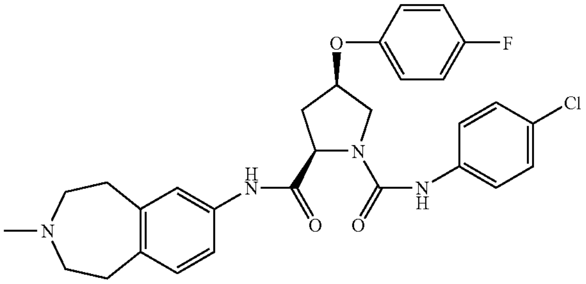 (2R,4R)-4-(4-fluorophenyl)oxy-pyrrolidine-1,2-dicarboxylic acid-1-N-(4-chloro-phenyl)amide-2-(3-methyl-2,3,4,5-tetrahydro-1H-benzo[d]azepin-7-yl)-amide | $(M + H)^+$ = 537/539 chlorine isotopes | |
| 40 | 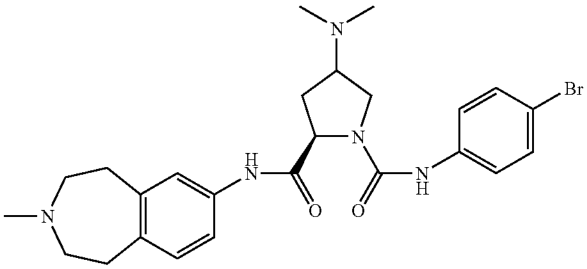 (2R)-4-dimethylamino-pyrrolidine-1,2-dicarboxylic acid-1-N-(4-bromo-phenyl)amide-2-(3-methyl-2,3,4,5-tetrahydro-1H-benzo[d]azepin-7-yl)-amide (2 stereoisomers) | $(M + H)^+$ = 514/516 bromine isotopes | $R_f$-value: 0.21 (silica gel; dichloromethane/ethanol/-ammonia = 80:20:2) |

-continued

| Ex. | Structural formula | Mass peak(s) | DC/HPLC |
|---|---|---|---|
| 41 | 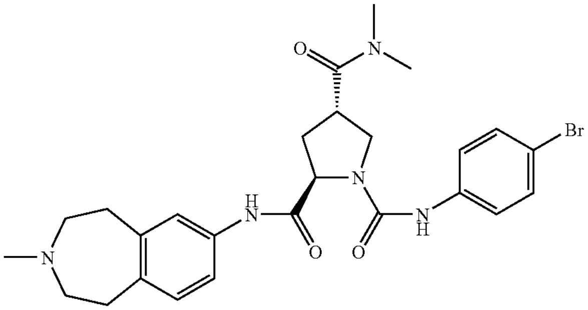<br>(2R,4S)-4-dimethylaminocarbonyl-pyrrolidine-1,2-dicarboxylic acid-1-N-(4-bromo-phenyl)amide-2-(3-methyl-2,3,4,5-tetrahydro-1H-benzo[d]azepin-7-yl)-amide | $(M + H)^+$ = 542/544 bromine isotopes | $R_f$-value: 0.55 (silica gel; dichloromethane/ethanol/-ammonia = 80:20:2) |
| 42 | 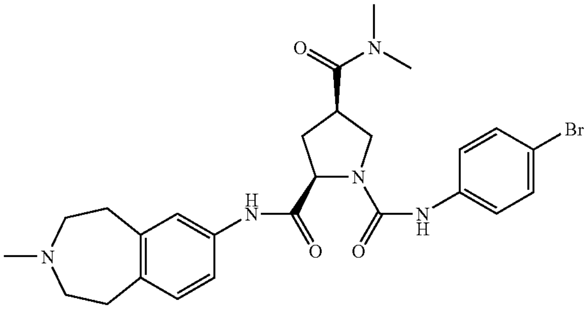<br>(2R,4R)-4-dimethylaminocarbonyl-pyrrolidine-1,2-dicarboxylic acid-1-N-(4-bromo-phenyl)amide-2-(3-methyl-2,3,4,5-tetrahydro-1H-benzo[d]azepin-7-yl)-amide | $(M + H)^+$ = 542/544 bromine isotopes | $R_f$-value: 0.45 (silica gel; dichloromethane/ethanol/-ammonia = 80:20:2) |
| 43 | 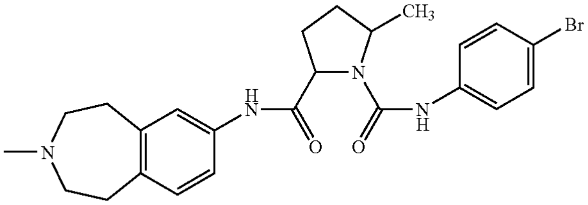<br>5-methyl-pyrrolidine-1,2-dicarboxylic acid-1-N-(4-bromo-phenyl)amide-2-(3-methyl-2,3,4,5-tetrahydro-1H-benzo[d]azepin-7-yl)-amide (stereoisomers) | $(M + H)^+$ = 485/587 bromine isotopes | |
| 44 | 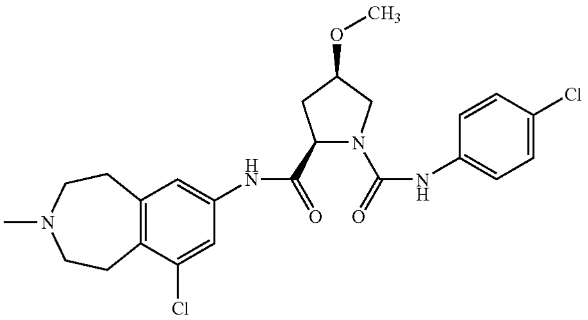<br>(2R,4R)-4-methyloxy-pyrrolidine-1,2-dicarboxylic acid-1-N-(4-chloro-phenyl)amide-2-(9-chloro-3-methyl-2,3,4,5-tetrahydro-1H-benzo[d]azepin-7-yl)-amide | $(M + H)^+$ = 491/493/495 chlorine isotopes | $R_f$-value: 0.33 (RP-8; methanol/5% NaCl soln. = 6/4) |
| 45 | 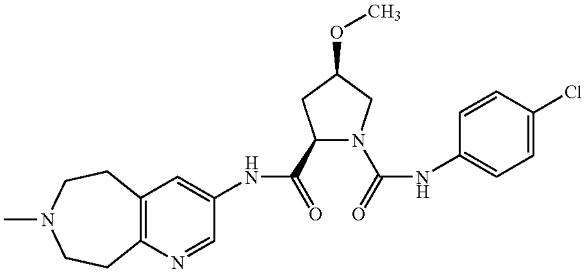 | $(M + H)^+$ = 458/460 chlorine isotopes | |

-continued
| Ex. | Structural formula | Mass peak(s) | DC/HPLC |
| --- | --- | --- | --- |
| 46 | 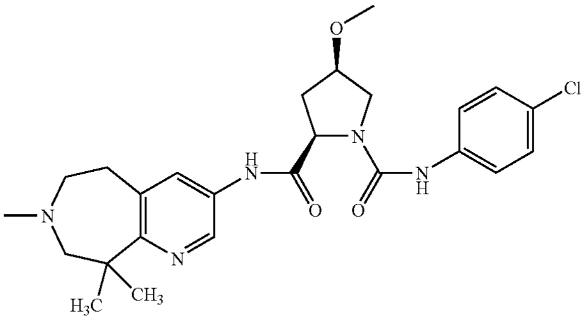 (2R,4R)-4-methyloxy-pyrrolidine-1,2-dicarboxylic acid-1-N-(4-chloro-phenyl)amide-2-(1.1,3-trimethyl-2,3,4,5-tetrahydro-1H-benzo[d]azepin-7-yl)-amide | $(M + H)^+$ = 485/487 chlorine isotopes | |
The following compounds may be prepared analogously:
A
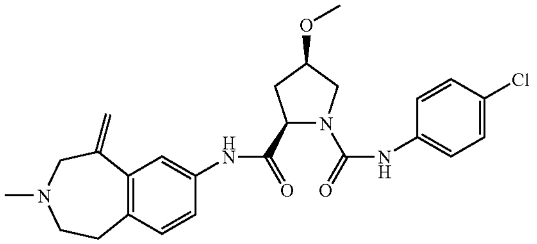
B
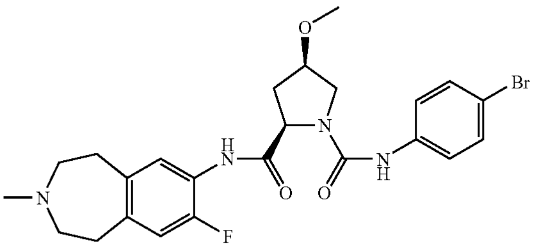
C
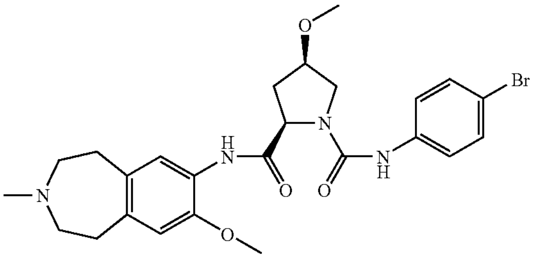
D
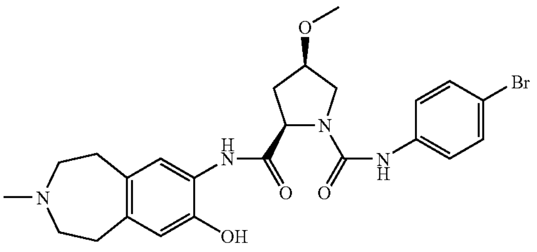
-continued
E
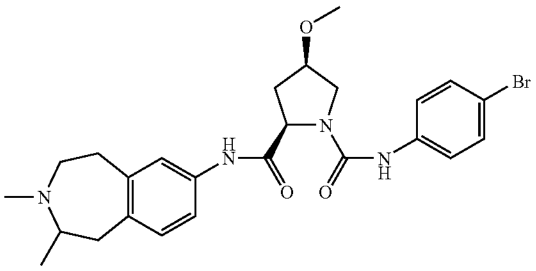
F
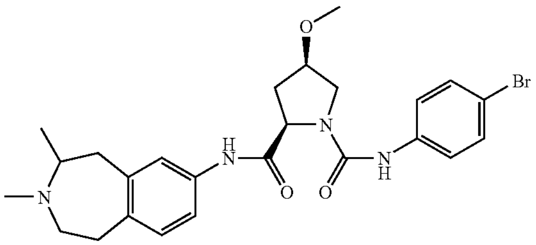
G
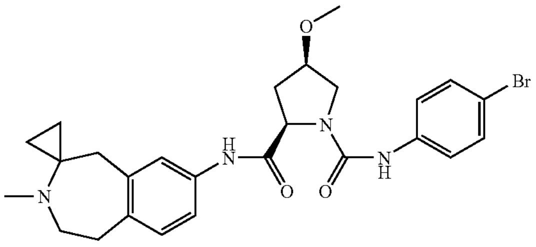
H
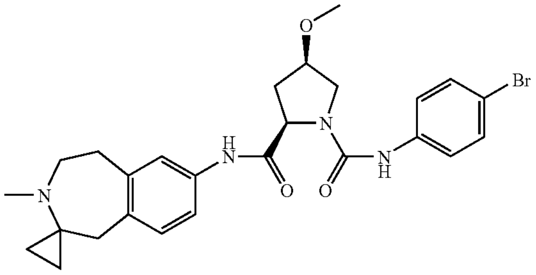

-continued

I

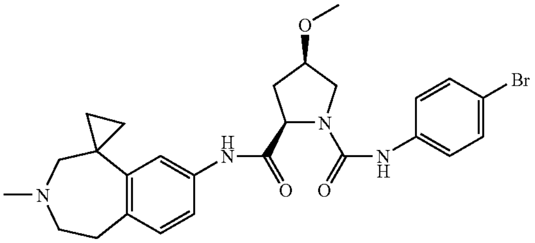

J

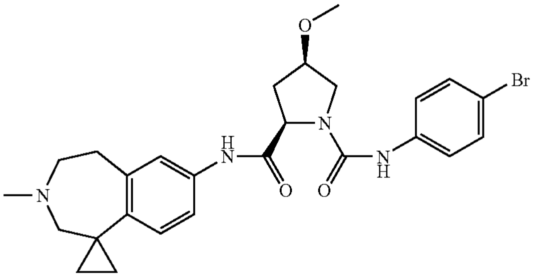

K

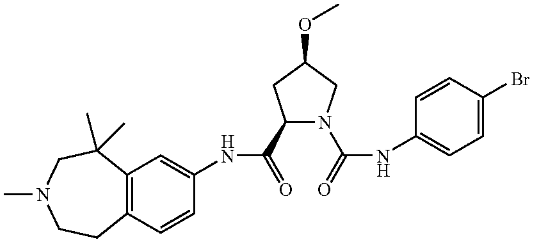

L

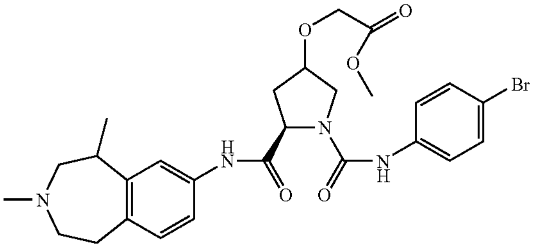

M

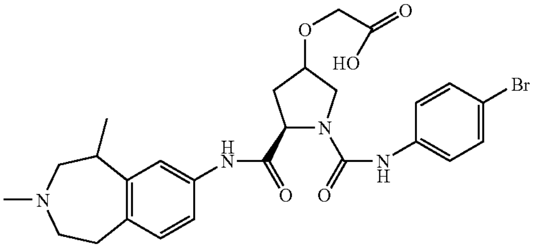

N

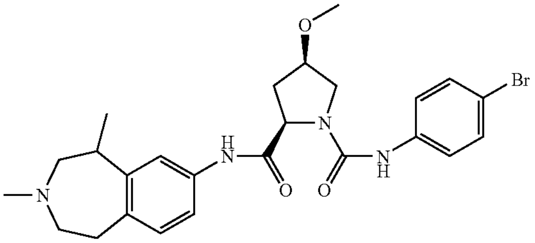

-continued

O

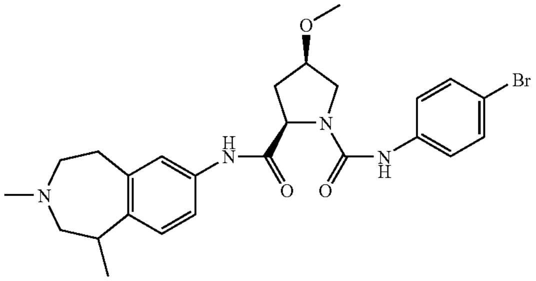

The Examples that follow describe the preparation of some pharmaceutical formulations which contain as active substance any desired compound of general formula I:

Example A

| Dry ampoule containing 75 mg of active substance per 10 ml Composition: | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

Example B

| Dry ampoule containing 35 mg of active substance per 2 ml Composition: | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

Example C

| Tablet containing 50 mg of active substance Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example D

| Tablet containing 350 mg of active substance Composition: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example E

| Capsules containing 50 mg of active substance Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

Example F

| Capsules containing 350 mg of active substance Composition: | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

Example G

| Suppositories containing 100 mg of active substance 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

The invention claimed is:

1. A compound of formula (I)

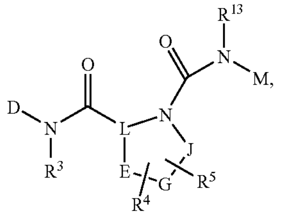

(I)

wherein

D denotes a substituted bicyclic ring system of formula (II)

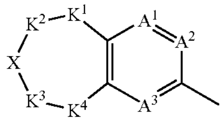

(II)

wherein $K^1$ and $K^4$ each independently of one another denote a —$CH_2$, —$CHR^{7a}$, —$CR^{7b}R^{7c}$, —C(=CH2) or a —C(O) group, and wherein $R^{7a}/R^{7b}/R^{7c}$ each independently of one another denote a fluorine atom, a hydroxy, $C_{1-5}$-alkyloxy, amino, $C_{1-5}$-alkylamino, di-($C_{1-5}$-alkyl)-amino, $C_{3-5}$-cycloalkyleneimino, $C_{1-5}$-alkylcarbonylamino group, a $C_{3-5}$-cycloalkyl or a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, while the two groups $R^{7b}/R^{7c}$ cannot both simultaneously be bound to the cyclic carbon atom via a heteroatom, except where —C($R^{7b}R^{7c}$)-corresponds to a —$CF_2$ group, or $R^{7a}$ denotes a phenyl or monocyclic heteroaryl group each optionally substituted with a fluorine-, chlorine-, bromine-, methyl-, methoxy-, amino- or nitro-group, or two groups $R^{7b}/R^{7c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylenesulphide, hexamethyleneimine, 1,3-dioxolane, 1,4-dioxane, hexahydropyridazine, piperazine, thiomorpholine, morpholine, 2-imidazolidinone, 2-oxazolidinone, tetrahydro-2(1H)-pyrimidinone or [1,3]oxazinan-2-one ring, the methylene groups of which may be substituted by 1-2 $C_{1-3}$-alkyl or $CF_3$-groups, and/or the methylene groups of which, if they are not bound to a heteroatom, may be substituted by 1-2 fluorine atoms, and/or wherein a —$CH_2$ group adjacent to an N atom may be replaced by a —CO group, and/or the imino groups of which may in each case be substituted by a $C_{1-3}$-alkyl or $C_{1-3}$-alkylcarbonyl group, and/or wherein the sulphur atom may be oxidised to a sulphoxide or sulphone group, $K^2$ and $K^3$ each independently of one another denote a —$CH_2$, —$CHR^{8a}$, —$CR^{8b}R^{8c}$ or a —C(O) group, wherein $R^{8a}/R^{8b}/R^{8c}$ each independently of one another denote a $C_{3-5}$-cycloalkyl or a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group, or two groups $R^{8b}/R^{8c}$ together with the cyclic carbon atom may form a 3-, 4-, 5-, 6- or 7-membered saturated carbocyclic group or a cyclopentene, cyclohexene, oxetane, azetidine, thietane, tetrahydrofuran, pyrrolidine, tetrahydrothiophene, tetrahydropyran, piperidine, pentamethylenesulphide, hexamethyleneimine, hexahydropyridazine, tetrahydro-2(1H)-pyrimidinone, [1,3]oxazinan-2-one ring, the methylene groups of which may be substituted by 1-2 $C_{1-3}$-alkyl or $CF_3$-groups, and/or the methylene groups of which, if they are not bound to a heteroatom, may be substituted by 1-2 fluorine atoms, and/or wherein a —$CH_2$ group adjacent to a nitrogen atom may be replaced by a —CO group, and/or the imino groups of which may in each case be substituted by a $C_{1-3}$-alkyl or $C_{1-3}$-alkylcarbonyl group, and/or wherein the sulphur atom may be oxidised to a sulphoxide or sulphone group, with the proviso that a heteroatom introduced by $R^{8b}$ or $R^{8c}$ must not be only one carbon atom away from X in formula (I), and in total a maximum of four groups selected from $R^{7a}$, $R^{7b}$, $R^{7c}$, $R^{8a}$, $R^{8b}$ and $R^{8c}$ may be present in formula (II), and X denotes a $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$, $C_{3-6}$-cycloalkyl, $C_{4-6}$-cycloalkenyl, oxetane-3-yl, tetrahydrofuran-3-yl, benzyl, $C_{1-5}$-alkyl-carbonyl, trifluoromethylcarbonyl, $C_{3-6}$-cycloalkyl-carbonyl, $C_{1-5}$-alkyl-sulphonyl, $C_{3-6}$-cycloalkyl-sulphonyl, aminocarbonyl, $C_{1-5}$-alkylaminocarbonyl, di-($C_{1-5}$-alkyl)-aminocarbonyl, $C_{1-5}$-alkyloxycarbonyl, $C_{4-7}$-cycloalkyleneiminocarbonyl group, while the methylene and methyl groups present in the groups mentioned previously may additionally be substituted by a $C_{1-3}$alkyl, carboxy or $C_{1-5}$-alkoxycarbonyl group, or by a hydroxy, $C_{1-5}$-alkyloxy, amino, $C_{1-5}$-alkylamino, $C_{1-5}$-dialkylamino or $C_{4-7}$-cycloalkyleneimino group, provided that the methylene or methyl groups are not bound directly to a heteroatom selected from among O, N or S, and/or one to three hydrogen atoms may be replaced by fluorine atoms, provided that the methylene or methyl groups are not bound directly to a heteroatom selected from among O, N or S, and wherein $A^1$ denotes $CR^{10}$, $A^2$ denotes $CR^{11}$, $A^3$ denotes $CR^{12}$, while $R^{10}$, $R^{11}$ and $R^{12}$ each independently of one another denote a hydrogen, fluorine, chlorine, bromine or iodine atom, or a $C_{1-5}$-alkyl, $CF_3$, $C_{2-5}$-alkenyl, $C_{2-5}$-alkynyl, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group, $R^3$ denotes a hydrogen atom or a $C_{1-3}$-alkyl group, and -L-E-G-J- denotes a —C—C—C—C or —C—C═C—C group, and $R^4$ denotes a hydrogen atom or a straight-chain or branched $C_{1-6}$-alkyl, $C_{2-6}$-alkenyl or $C_{2-6}$-alkynyl group, wherein the hydrogen atoms of the methylene and/or methyl fragments of the straight-chain or branched $C_{1-6}$-alkyl, $C_{2-6}$-alkenyl or $C_{2-6}$-alkynyl group may optionally be replaced by one or more fluorine atoms, and/or wherein the hydrogen atoms of the methylene and/or methyl fragments of the straight-chain or branched $C_{1-6}$-alkyl, $C_{2-6}$-alkenyl or $C_{2-6}$-alkynyl group may optionally each be replaced independently of one another by one to two substituents selected from a $C_{3-5}$-cycloalkyl group, a nitrile, hydroxy or $C_{1-5}$-alkyloxy group, wherein the hydrogen atoms of the $C_{1-5}$-alkyloxy group may optionally be replaced by one or more fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, aminosulphonyl, $C_{1-5}$-alkylaminosulphonyl, di-($C_{1-5}$-alkyl)-aminosulphonyl, $C_{4-7}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino, $C_{3-6}$-cycloalkylcarbonylamino group, or a morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 $C_{1-3}$-alkyl or $C_{1-3}$-alkylcarbonyl groups or by 1-2 oxo groups, and/or wherein the hydrogen atoms of the $sp^2$-hybridised carbon atoms of the straight-chain or branched $C_{2-6}$-alkenyl group may optionally be replaced by one or more fluorine atoms, or a nitrile, carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, or a phenyl, mono- or bicyclic heteroaryl, phenyl-$C_{1-5}$-alkyl or mono- or bicyclic heteroaryl-$C_{1-5}$-alkyl group, which may optionally be mono- to tri-substituted in the phenyl or heteroaryl moiety by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy and $C_{1-5}$-alkyloxycarbonyl group, and if -L-E-G-J- denotes a —C—C—C—C group, $R^4$ at E or G may also denote a fluorine atom or a hydroxy, $C_{2-5}$-alkenyloxy, $C_{2-5}$-alkynyloxy, $C_{1-5}$-alkyl-oxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, heteroaryl-$C_{0-3}$-alkyloxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonyl-amino group, while the methyl or methylene groups present in the above-mentioned alkyl or cycloalkyl groups may each be substituted independently of one another by a substituent selected from among morpholinyl, thiomorpholinyl, pyrrolidinyl, piperidinyl, piperazinyl, tetrahydrofuranyl, tetrahydropyranyl, dimethylaminocarbonyl, $C_{1-3}$alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or that two atoms form an —O—O or —S—O— bond, is excluded, and $R^5$ denotes a hydrogen atom or a $C_{1-5}$ alkyl, $C_{2-5}$ alkenyl or $C_{2-5}$ alkynyl group, or if $R^5$ is linked to E or G it may also denote a hydroxy or methoxy group, or $R^4$ and $R^5$ if they are bound to the same carbon atom, may form a —C(O)— group, or a —C($F_2$)— group, or $R^4$ and $R^5$ if they are bound to the same carbon atom or to two adjacent carbon atoms, may form a $C_{3-7}$-cycloalkyl or $C_{5-7}$-cycloalkenyl group, wherein one of the methylene groups of this $C_{3-7}$-cycloalkyl group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or wherein two directly adjacent methylene groups of this $C_{3-7}$-cycloalkyl group may together be replaced by a —C(O)NH, —C(O)N($C_{1-5}$-alkyl), —$S(O)_2$NH, or —$S(O)_2$N($C_{1-5}$-alkyl) group, and/or wherein 1 to 3 carbon atoms of a $C_{3-7}$-cycloalkyl group may each optionally be substituted independently of one another by one or two fluorine atoms or one or two $C_{1-5}$-alkyl groups or a hydroxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group, with the proviso that a $C_{3-7}$-cycloalkyl group of this kind, formed from $R^4$ and $R^5$ together, wherein two heteroatoms in the cyclic group selected from among oxygen and nitrogen are separated from one another by precisely one optionally substituted —$CH_2$ group, and/or wherein two atoms in the ring form a —O—O or —S—O— bond, is excluded, $R^{13}$ denotes a hydrogen atom or a $C_{1-5}$ alkyl group, M denotes a phenyl, thienyl or pyridyl ring optionally substituted by $R^2$ and $R^6$, wherein $R^2$ denotes a fluorine, chlorine, bromine or iodine atom or a methyl, ethyl, propyl, isopropyl, vinyl, methoxy, ethynyl, cyano or —C(O)$NH_2$ group, and $R^6$ denotes a hydrogen, fluorine, chlorine, bromine or iodine atom or a hydroxy, methoxy, trifluoromethoxy, an optionally fluorine-substituted $C_{1-3}$-alkyl, cyano, amino, or $NH_2$C(O) group, while, unless otherwise stated, by the term "heteroaryl group" mentioned hereinbefore in the definitions is meant a monocyclic 5- or 6-membered heteroaryl group wherein the 6-membered heteroaryl group contains one, two or three nitrogen atoms, and the 5-membered heteroaryl group contains an imino group optionally substituted by a $C_{1-3}$-alkyl group, an oxygen or sulphur atom, or an imino group optionally substituted by a $C_{1-3}$-alkyl group or an oxygen or sulphur atom and additionally one or two nitrogen atoms, or an imino group optionally substituted by a $C_{1-3}$-alkyl group and three nitrogen atoms, and additionally a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms, via a nitrogen atom or a carbon atom of the heterocyclic moiety or a fused-on phenyl ring, and wherein, unless otherwise stated, by the term "halogen atom" mentioned hereinbefore in the definitions is meant an atom selected from among fluorine, chlorine, bromine and iodine, and wherein unless stated otherwise the alkyl, alkenyl, alkynyl and alkoxy groups which have more than two carbon atoms, contained in the foregoing definitions, may be straight-chain or branched and the alkyl groups in the previously mentioned dialkylated groups may be identical or different, and the hydrogen atoms of the methyl or ethyl groups contained in the foregoing definitions, unless stated otherwise, may be replaced by one or more fluorine atoms, or a tautomer, enantiomer, diastereomer, a mixture thereof or a pharmaceutically acceptable salt thereof.

2. A compound of formula (I) according to claim 1, wherein

D denotes a substituted bicyclic ring system of formula (II)

(II)

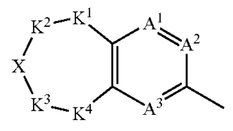

wherein $K^1$ and $K^4$ each independently of one another denote a —$CH_2$, —$CHR^{7a}$, —$CR^{7b}R^{7c}$, —C(=CH2) or a —C(O) group, and wherein $R^{7a}/R^{7b}/R^{7c}$ each independently of one another denote a fluorine atom, a hydroxy, $C_{1-5}$-alkyloxy, a $C_{1-5}$-alkyl group, while the two groups $R^{7b}/R^{7c}$ cannot both simultaneously be bound to the cyclic carbon atom via a heteroatom, except where —$C(R^{7b}R^{7c})$-corresponds to a —$CF_2$ group, or two groups $R^{7b}/R^{7c}$ together with the cyclic carbon atom may form a cyclopropyl ring, $K^2$ and $K^3$ each independently of one another denote a —$CH_2$, —$CHR^{8a}$, —$CR^{8b}R^{8c}$ or a —C(O)— group, while $R^{8a}/R^{8b}/R^{8c}$ each independently of one another denote a $C_{1-5}$-alkyl group, or two groups $R^{8b}/R^{8c}$ together with the cyclic carbon atom may form a cyclopropyl ring, and in total a maximum of four groups selected from $R^{7a}$, $R^{7b}$, $R^{7c}$, $R^{8a}$, $R^{8b}$ and $R^{8c}$ may be present in formula (II), and X denotes a $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$ or a $C_{3-6}$-cycloalkyl group, and wherein $A^1$ denotes $CR^{10}$, $A^2$ denotes $CR^{11}$, $A^3$ denotes $CR^{12}$, while $R^{10}$, $R^{11}$ and $R^{12}$ each independently of one another denote a hydrogen, fluorine, chlorine, bromine or iodine atom, or a $C_{1-5}$-alkyl, $CF_3$, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group.

3. A compound of formula (I) according to claim 1, wherein

X denotes a $NR^1$ group, wherein $R^1$ denotes a hydrogen atom or a $C_{1-5}$-alkyl, allyl or cyclopropyl group, and $A^1$ denotes $CR^{10}$, $A^2$ denotes $CR^{11}$, $A^3$ denotes $CR^{12}$, while $R^{10}$, $R^{11}$ and $R^{12}$ each independently of one another represent a hydrogen, fluorine or chlorine atom, or a methyl, $CF_3$, hydroxy, methoxy, $CF_3O$, $CHF_2O$, $CH_2FO$ group.

4. A compound of formula (I) according to claim 1, wherein $R^4$ denotes a hydrogen atom or a straight-chain or branched $C_{1-6}$-alkyl group, wherein the hydrogen atoms of the methylene and/or methyl fragments of the straight-chain or branched $C_{1-6}$-alkyl group may optionally be replaced by one or more fluorine atoms, and/or wherein the hydrogen atoms of the methylene and/or methyl fragments of the straight-chain or branched $C_{1-6}$-alkyl group may optionally each be replaced independently of one another by a substituent selected from a hydroxy, $C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N-($C_{1-5}$-alkylsulphonyl)-$C_{1-5}$-alkylamino, $C_{3-6}$-cycloalkylcarbonylamino group, or a nitrile, carboxy, aminocarbonyl, $C_{1-5}$-alkylaminocarbonyl, $C_{3-6}$-cycloalkylamino-carbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by an oxygen, sulphur or $C_{0-3}$-alkyl-substituted nitrogen atom, and if -L-E-G-J- denotes a —C—C—C—C group, $R^4$ at E or G may also denote a fluorine atom or a hydroxy, methoxy, $C_{2-5}$-alkenyloxy, $C_{2-5}$-alkynyloxy, $C_{1-5}$-alkyl-oxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl) aminocarbonylamino or a $C_{4-7}$-cycloalkyleneiminocarbonylamino-group, while the methyl or methylene groups present in the above-mentioned alkyl or cycloalkyl groups may each be substituted independently of one another by a substituent selected from among dimethylaminocarbonyl, $C_{1-3}$alkyloxycarbonyl, carboxy, methyl, hydroxy, methoxy or amino, with the proviso that two heteroatoms selected from among oxygen and nitrogen are separated from one another by precisely one optionally substituted —$CH_2$ group, and/or that two atoms form an —O—O or —S—O— bond, is excluded, and $R^5$ denotes a hydrogen atom, an allyl or a $C_{1-5}$ alkyl group, or if $R^5$ is linked to E or G it may also denote a hydroxy or methoxy group or $R^4$ and $R^5$, if they are bound to the same carbon atom, may form a —C(O)— group, or a —$C(F_2)$— group, or $R^4$ and $R^5$ if they are bound to the same carbon atom or to two adjacent carbon atoms, may form a $C_{3-7}$-cycloalkyl group, wherein one of the methylene groups of this $C_{3-7}$-cycloalkyl group may be replaced by an oxygen or sulphur atom or an —NH, —N($C_{1-5}$-alkyl), —N($C_{1-4}$-alkylcarbonyl) or a carbonyl, sulphinyl or sulphonyl group, and/or wherein two directly adjacent methylene groups of this $C_{3-7}$-cycloalkyl group may together be replaced by a —C(O)NH, —C(O)N($C_{1-5}$-alkyl), —$S(O)_2NH$ or —$S(O)_2N$($C_{1-5}$-alkyl) group.

5. A compound of formula (I) according to claim 1, wherein -L-E-G-J- denotes a —C—C—C—C group.

6. A compound of formula (I) according to claim 1, wherein

D denotes a substituted benzazepinyl group of formula (IIa)

(IIa)

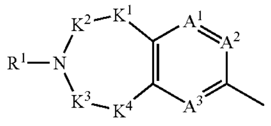

wherein $K^1$ and $K^4$ each independently of one another denote a —$CH_2$, —$CHR^{7a}$, —$CR^{7b}R^{7c}$ or a —C(O) group, wherein $R^{7a}$ denotes a $C_{1-5}$-alkyl, hydroxy or $C_{1-3}$-alkyloxy group and $R^{7b}/R^{7c}$ each independently of one another denote a hydroxy, $C_{1-5}$-alkyloxy or a $C_{1-5}$-alkyl group, while the two groups $R^{7b}/R^{7c}$ cannot both simultaneously be bound to the cyclic carbon atom via an oxygen atom, or two groups $R^{7b}/R^{7c}$ together with the cyclic carbon atom may form a cyclopropyl ring, and $K^2$ and $K^3$ each independently of one another denote a —$CH_2$, —$CHR^{8a}$ or —$CR^{8b}R^{8c}$ group, wherein $R^{8a}/R^{8b}/R^{8c}$ each independently of one another denote a $C_{1-3}$-alkyl group, and in total a maximum of four groups selected from $R^{7a}$, $R^{7b}$, $R^{7c}$, $R^{8a}$, $R^{8b}$ and $R^{8c}$ may be present in formula (II), and $R^1$ denotes a hydrogen atom or a $C_{1-5}$-alkyl, allyl or cyclopropyl group, and $A^1$ denotes $CR^{10}$, $A^2$ denotes $CR^{11}$, $A^3$ denotes $CR^{12}$, while $R^{10}$, $R^{11}$ and $R^{12}$ each independently of one another denote a hydrogen, fluorine or chlorine atom, or a methyl, $CF_3$, hydroxy, methoxy, $CF_3O$, $CHF_2O$, $CH_2FO$ group, and -L-E-G-J- denotes a —C—C—C—C group, and $R^3$ denotes a hydrogen atom, and $R^4$ denotes a hydrogen atom or a straight-chain or branched $C_{1-3}$-alkyl group, wherein the hydrogen atoms of the methylene and/or methyl fragments of the straight-chain or branched $C_{1-6}$-alkyl group may optionally be replaced independently of one another by a substituent selected from among a hydroxy, $C_{1-5}$-alkyloxy, carboxy, $C_{1-5}$-alkyloxycarbonyl group, or a $CF_3$, nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group, or if $R^4$ is bound to E or G it may also denote a fluorine atom or a hydroxy, methoxy, $C_{2-5}$-alkenyl-oxy, $C_{2-5}$-alkyloxy, methoxyethoxy, $HOCH_2CH(OH)CH_2$oxy, $C_{3-6}$-cycloalkyloxy, $C_{1-5}$-alkylaminocarbonyloxy, di($C_{1-5}$-alkyl)aminocarbonyloxy or $C_{4-7}$-cycloalkyleneiminocarbonyloxy-group, $R^5$ denotes a hydrogen atom or a $C_{1-5}$ alkyl group, or if $R^5$ is linked to E or G it may also denote a hydroxy or methoxy group, or $R^4$ and $R^5$, if they are bound to the same carbon atom, may denote a C═O or a —$CF_2$ group, and $R^{13}$ denotes a hydrogen atom, M denotes a substituted phenyl ring

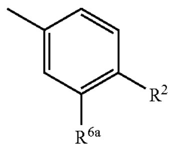

or a substituted pyridyl ring

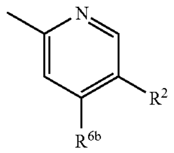

wherein $R^2$ denotes a fluorine, chlorine, bromine atom, a methoxy or ethynyl group, and $R^{6a}$ denotes a hydrogen or fluorine atom and $R^{6b}$ denotes a hydrogen atom.

7. A pharmaceutically acceptable salt according to claim 1.

8. A pharmaceutical composition comprising a compound according to claim 1 and one or more inert carriers and/or diluents.

9. A process for preparing a pharmaceutical composition comprising incorporating a compound according to claim 1 in one or more inert carriers and/or diluents by a non-chemical method.

10. A pharmaceutical composition comprising a physiologically acceptable salt according to claim 7 and one or more inert carriers and/or diluents.

11. A process for preparing a pharmaceutical composition comprising incorporating a pharmaceutically acceptable salt according to claim 7 in one or more inert carriers and/or diluents by a non-chemical method.

* * * * *